United States Patent
Ray, II

(10) Patent No.: US 11,690,815 B2
(45) Date of Patent: *Jul. 4, 2023

(54) HYPERKERATOTIC SKIN CONDITION TREATMENTS AND COMPOSITIONS

(71) Applicant: CMPD LICENSING, LLC, Conroe, TX (US)

(72) Inventor: Jay Richard Ray, II, Conroe, TX (US)

(73) Assignee: CMPD LICENSING LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/970,340

(22) Filed: May 3, 2018

(65) Prior Publication Data

US 2018/0250248 A1 Sep. 6, 2018

Related U.S. Application Data

(63) Continuation-in-part of application No. 14/990,168, filed on Jan. 7, 2016, and a continuation-in-part of application No. 15/597,936, filed on May 17, 2017, now Pat. No. 10,105,342, and a continuation-in-part of application No. 15/668,184, filed on Aug. 3, 2017, said application No. 15/597,936 is a continuation-in-part of application No. 15/440,800, filed on Feb. 23, 2017, and a continuation-in-part of application No. 14/975,172, filed on Dec. 18, 2015, now Pat. No. 9,707,229, and a continuation-in-part of application No. 14/819,342, filed on Aug. 5, 2015.

(60) Provisional application No. 62/298,994, filed on Feb. 23, 2016, provisional application No. 62/298,991, filed on Feb. 23, 2016, provisional application No. 62/370,571, filed on Aug. 3, 2016.

(51) Int. Cl.
- *A61K 31/17* (2006.01)
- *A61K 9/00* (2006.01)
- *A61K 31/58* (2006.01)
- *A61K 9/06* (2006.01)
- *A61K 31/573* (2006.01)

(52) U.S. Cl.
CPC ............ *A61K 31/17* (2013.01); *A61K 9/0014* (2013.01); *A61K 9/06* (2013.01); *A61K 31/573* (2013.01); *A61K 31/58* (2013.01)

(58) Field of Classification Search
CPC .......... A61K 31/17; A61K 9/06; A61K 31/58; A61K 31/573; A61K 9/0014
See application file for complete search history.

(56) References Cited

U.S. PATENT DOCUMENTS

| | | | |
|---|---|---|---|
| 2,989,965 A | 6/1961 | Rod | |
| 5,324,746 A | 6/1994 | McKee et al. | |
| 5,710,280 A | 1/1998 | Shih et al. | |
| 6,143,794 A | 11/2000 | Chaudhuri et al. | |
| 6,197,830 B1 | 3/2001 | Frame | |
| 6,365,635 B1 | 4/2002 | Nomura | |
| 9,078,853 B2 | 7/2015 | Ray | |
| 9,707,229 B2 | 7/2017 | Ray | |
| 9,717,748 B2 | 8/2017 | Ray | |
| 10,105,342 B2 | 10/2018 | Ray | |
| 2002/0061281 A1 | 5/2002 | Osbakken et al. | |
| 2003/0091519 A1 | 5/2003 | Zatz et al. | |
| 2003/0143162 A1 | 7/2003 | Speirs et al. | |
| 2003/0226201 A1 | 12/2003 | Leung et al. | |
| 2004/0033963 A1 | 2/2004 | Yu et al. | |
| 2004/0151765 A1 | 8/2004 | Ritchie | |
| 2004/0191329 A1 | 9/2004 | Burrell et al. | |
| 2005/0043251 A1 | 2/2005 | Lane | |
| 2005/0137164 A1 | 6/2005 | Arkin | |
| 2005/0255048 A1 | 11/2005 | Hirsh et al. | |
| 2006/0246098 A1 | 11/2006 | Rao et al. | |
| 2009/0016990 A1 | 1/2009 | Alberte et al. | |
| 2010/0081669 A1 | 4/2010 | Yang et al. | |
| 2011/0105448 A1 | 5/2011 | Dhuppad et al. | |
| 2012/0328671 A1 | 12/2012 | O'Neil et al. | |

(Continued)

FOREIGN PATENT DOCUMENTS

| | | |
|---|---|---|
| JP | H0774144 | 8/1995 |
| WO | 2006060027 | 6/2006 |
| WO | 2014167554 | 10/2014 |

OTHER PUBLICATIONS

JPH0774144B2, English Translation from Espacenet Patent Translate powered by EPO and Google, Aug. 1995, 5 pages (Year: 1995).*

Jacoby, R.H., A New Urea/Hydrocortisone Powder-Cream Compared with other Topical Corticosteroid Preparations: A Six-Center Study, 1974, Current Medical Research and Opinion, vol. 2, No. 8, pp. 474-481. (Year: 1974).*

(Continued)

*Primary Examiner* — Monica A Shin

(74) *Attorney, Agent, or Firm* — Akerman LLP

(57) ABSTRACT

A method of treating a hyperkeratotic skin condition includes combining contents of a compounded capsule with corticosteroid cream or ointment that includes a high potency corticosteroid to formulate a topical composition for application to a skin area affected by hyperkeratosis. The contents of the capsule may include urea powder, and the corticosteroid cream or ointment may include Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, or a combination thereof.

4 Claims, No Drawings

(56) References Cited

U.S. PATENT DOCUMENTS

| | | | |
|---|---|---|---|
| 2013/0072563 | A1 | 3/2013 | Ho |
| 2014/0256826 | A1 | 9/2014 | Lemire et al. |
| 2015/0320816 | A1 | 11/2015 | Patel |
| 2016/0166505 | A1 | 6/2016 | Ray |
| 2017/0035736 | A1 | 2/2017 | Ray |
| 2017/0173063 | A1 | 6/2017 | Ray |
| 2017/0196823 | A1 | 7/2017 | Ray |
| 2017/0239277 | A1 | 8/2017 | Ray |
| 2017/0246140 | A1 | 8/2017 | Ray |
| 2017/0312276 | A1 | 11/2017 | Ray |
| 2017/0326167 | A1 | 11/2017 | Ray |
| 2017/0333464 | A1 | 11/2017 | Ray |
| 2017/0333467 | A1 | 11/2017 | Ray |
| 2018/0036227 | A1 | 2/2018 | Ray |
| 2018/0147211 | A1 | 5/2018 | Ray |
| 2018/0147212 | A1 | 5/2018 | Ray |
| 2018/0256675 | A1 | 9/2018 | Ray |

OTHER PUBLICATIONS

Clobetasol Propionate Cream, USP 0.05% and Clobetasol Propionate Ointment, USP 0.05%. Information Sheet [online]. DailyMed.nlm.nih.gov, 2012, [retrieved on Mar. 11, 2020]. Retrieved from the Internet:<URL:https://dailymed.nlm.nih.gov/dailymed/fda/fdaDrugXsl.cfm?setid=b6575dd5-afa3-433b-860f-6d61cf8796a1>(Year: 2012).*

Urea Cream. Formulation Record. [online]. Pharmlabs UNC, 2003 [retrieved on Sep. 24, 2020]. Retrieved from the Internet: <URL:https://pharmlabs.unc.edu/labs/formulation_records/urea_cream_form.pdf>. (Year: 2003).*

Urea Powder, Technical Grade. [online]. Rose Mill Chemicals and Lubricants, 2009, [retrieved on Sep. 24, 2020]. Retrieved from the Internet: <URL:https://rosemill.com/wp-content/uploads/2018/02/ureapowder.pdf>. (Year: 2009).*

Medinvent, "The NasoNeb Nasal Nebulizer", Nov. 15, 2013.

Sutherland et al., "Antimicrobial Agents and Chemotherapy," 1985, vol. 27, pp. 495-498.

Balzarini et al., "Lancet", 2007, vol. 369, pp. 787-797.

Allen US Pharm., 2011, vol. 36(6), pp. 44-45.

Lewandowksi et al., "Military Medicine", 2013, vol. 178, pp. e503-e507.

BACTROBAN® Ointment (mupirocin ointment, 2%) Prescribing Information, GlaxoSmithKline, Revised May 2014 (17 pages).

ATICLATE® (Doxycycline Hyclate Tablets), Final Labeling Text, Aqua Pharmaceuticals, Revised Jul. 2014 (18 pages).

Ketoconazole Human Prescription Drug Label; Physician's Desk Reference, Ver. 1—Published Feb. 2007 (5 pages).

Tobramycin Human Prescription Drug Label; Physician's Desk Reference, Ver. 1—Published May 2014 (9 pages).

Ciprofloxacin Human Prescription Drug Label; Physician's Desk Reference, Ver. 1—Published Feb. 2010 (19 pages) (hereinafter Ciprofloxacin PDR).

Pan et al. Urea: a comprehensive review of the clinical literature. Dermatology Online Journal, 19(11), Nov. 2013. doj_20392. Retrieved from: http://escholarship.org/uc/item/11x463rp.

Shah, "Urea ointment (40%)," Indian J Dermatol Venereol Leprol, 69:421-422, Nov. 25, 2015. Retrieved from http://www.ijdvl.com/text.asp?2003/69/6/421/663.

Taro Pharmaceuticals U.S.A., Inc., "U-CORT—hydrocortisone acetate cream," Mar. 2012, document of 6 pages.

PCCA, "Technical Report: Spira-Wash Gel™ Wound Care Base—an Antimicrobial Evaluation," Mar. 2014, document of 2 page.

Crown Laboratories, "REA LO 39—urea cream," Aug. 2014, document of 4 pages.

Stratus Pharmaceuticals, Inc., "Remeven—urea cream," May 2011, document of 5 pages.

Medimetriks Pharmaceuticals, Inc., "URAMAXIN GT—urea gel, URAMAXIN GT—uramaxin gt and keradan," Apr. 2012, document of 11 pages.

Medimetriks Pharmaceuticals, Inc., "URAMAXIN TS—urea cream," Apr. 2010, document of 6 pages.

Crown Laboratories, "REA LO 40—urea cream, REA LO 40—urea lotion," Aug. 2014, document of 7 pages.

Purvis, "Simultaneous High Performance Liquid Chromatography Assay of Pentoxifylline, Mupirocin, Itraconazole, and Fluticasone Propionate in Humco™ Lavare Wound Base," Chromatography 2015, 2, 642-654.

Humco, https://www.humco.com/pharmaceuticals/lavare/, accessed Oct. 1, 2017.

Roerig, "Diflucan-fluconazole tablet, Diflucan-fluconazole powder, for suspension," Pfizer, Mar. 2013, document of 61 pages.

PCCA, "LoxaSperse™, Powder Excipient Base for Use in Nebulization and Irrigation Compounds," 2013, document of 3 pages.

Pfizer, "Fluconazole Injection, USP, in INTRAVIA Plastic Container," Pfizer Injectables, Aug. 2010, document of 4 pages, https://www.pfizer.com/files/products/uspi_fluconazole.pdf.

PCCA XYIFOS Trademark Appl. No. 8842712 (May 27, 2015), pp. 1-8.

Freels, Lexington Podiatry (2011), pp. 1-2.

U.S. Appl. No. 14/819,342, filed Aug. 5, 2015, Applicant is CMPD Licensing, LLC, Inventor is Jay Richard Ray, II.

Label for DIFLUCAN (Fluconazole Tablets), Distributed by Roerig, a Division of Pfizer, Mar. 2013 (35 pages).

Label (Package Insert) for Azithromycin, Distributed by SICOR Pharmaceuticals, Inc., Dec. 2016 (18 pages).

Label for BACTROBAN (mupirocin), Distributed by GlaxoSmithKline, Dec. 2015 (10 pages).

FDA Prescribing Information for NYSTATIN Powder, Distributed by Mayne Pharma, Summarized by www.drugs.com (5 pages), no date provided Jun. 10, 2019.

PCCA, Brochure for LoxaSperse, "Powder Excipient Base for Use in Nebulization and Irrigation Compounds", 2013 (3 pages).

PCCA, "New, Exclusive PCCA Base, XyliFos™: Boost the LoxaSperse™ Power in Nasal Nebulization and Decrease your Cost", Aug. 7, 2015 (2 pages).

Bhapkar et al., IOSR Journal of Pharmacy (2013), vol. 3, pp. 24-48.

Angamuthu et al., Controlled-release injectable containing Terbinafine/PLGA microspheres for Onychomycosis Treatment, 2014, Journal of Pharmaceutical Sciences, vol. 103, pp. 1178-1183. (Year 2014).

Bae et al., Green Nail Syndrome Treated with the Applicatin of Tobramycin Eye Drop, 2014, Ann Dermatology, vol. 26, No. 4, pp. 514-516. (Year 2014).

QUIX® PDR, Vistakon Pharmaceuticals; 6 pages (Revised Mar. 2010). (Year 2010).

Kowalski et al., "Topical levofloxacin 1.5% overcomes in vitro resistance in rabbit keratitis models," Acta Ophthalmol. Jun. 2010; 88 (4): e120-e1251; cited as pp. 1-14. (Year 2010).

PCCA LoxaSperse Based Studies (2013 & 2014), pp. 1-12.

PCCA LoxaSperse, PCCA # 30-4701, 2013, pp. 1-2.

Beyonddisease.Com, "Does Bleach Kill Toenail Fungus? How to Use it?," 5 pages, available at http://www.beyonddisease.com/bleach-for-nail-fungus (published on Jun. 30, 2015).

Lee Silsby, "Loxasperse TM Formulations," 3 pages, webpage capture of http://leesilsby.com/loxasperseformulations on Oct. 17, 2014.

* cited by examiner

HYPERKERATOTIC SKIN CONDITION TREATMENTS AND COMPOSITIONS

CROSS-REFERENCE TO RELATED APPLICATIONS

The present application is a continuation-in-part of U.S. patent application Ser. No. 14/990,168, filed Jan. 7, 2016, U.S. patent application Ser. No. 15/597,936, filed May 17, 2017, and U.S. patent application Ser. No. 15/668,184, filed Aug. 3, 2017, each of which is hereby incorporated herein by reference. U.S. patent application Ser. No. 15/597,936 is a continuation-in-part application of U.S. patent application Ser. No. 15/440,800, filed Feb. 23, 2017, U.S. patent application Ser. No. 14/975,172, filed Dec. 18, 2015 (now U.S. Pat. No. 9,707,229), and U.S. patent application Ser. No. 14/819,342, filed Aug. 5, 2015, each of which is hereby incorporated herein by reference. U.S. patent application Ser. No. 15/440,800 claims priority under 35 U.S.C. § 119(e) to U.S. Provisional Patent Application No. 62/298,991, filed Feb. 23, 2016, and U.S. Provisional Patent Application No. 62/298,994, filed Feb. 23, 2016, each of which is hereby incorporated herein by reference. U.S. patent application Ser. No. 15/668,184 claims priority under 35 U.S.C. § 119(e) to U.S. Provisional Patent Application No. 62/370,571, filed on Aug. 3, 2016, which is hereby incorporated herein by reference.

TECHNICAL FIELD

The present application is directed to topical compositions. More specifically, the present application is directed to topical compositions containing urea and a corticosteroid.

BACKGROUND

Hyperkeratotic skin conditions are marked by a thickening of the outer layers of skin. While skin thickening causing common corns and calluses is a normal protection mechanism for skin, hyperkeratosis may result from irritations such as chemical contact, infections, and sunlight. Propensity for hyperkeratotic episodes may also be genetically linked, which may occur despite lack of abnormal irritation to the skin region. Individuals experiencing hyperkeratosis may experience discomfort, which may be accompanied by severe pain.

Treatments for hyperkeratosis include surgical removal, e.g., cryosurgery, scalpel, laser. Chronic eczema and lichen planus may be treated with a corticosteroid.

SUMMARY

In one aspect, a method of treating a hyperkeratotic skin condition includes combining contents of a compounded capsule with corticosteroid cream or ointment comprising a high potency corticosteroid to formulate a topical composition for application to a skin area affected by hyperkeratosis. The contents of the capsule comprises urea powder.

In various embodiments, the contents of the compounded capsule and the corticosteroid cream or ointment are combined in amounts sufficient to formulate the topical composition comprising between approximately 2.5% and approximately 50% urea by weight of the compounded composition and between approximately 0.001% and approximately 0.250% high potency corticosteroid by weight. In one embodiment, the corticosteroid cream or ointment comprises Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, or a combination thereof. In one example, the corticosteroid cream or ointment comprises Clobetasol Propionate Cream or Ointment, Desoximetasone Cream or Ointment, Fluocinonide Cream or Ointment, Halobetasol Propionate Cream, or a combination thereof.

In various embodiments, the corticosteroid cream or ointment comprises Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, Triamcinolone Acetonide Cream or Ointment, or a combination thereof. In a further example, the corticosteroid cream or ointment may include Betamethasone Dipropionate Cream or Ointment Clobetasol Propionate Cream or Ointment, Desoximetasone Cream or Ointment, Fluocinonide Cream or Ointment, Halobetasol Propionate Cream, Triamcinolone Acetonide Cream or Ointment, or a combination thereof.

In one embodiment, the contents of the compounded capsule and the corticosteroid cream or ointment are combined in amounts sufficient to formulate the topical composition comprising between approximately 10% and approximately 25% urea by weight and between approximately 0.025% and approximately 0.098% high potency corticosteroid by weight. In one example, the corticosteroid cream or ointment comprises Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, Triamcinolone Acetonide Cream or Ointment, or a combination thereof. In one embodiment, the corticosteroid cream or ointment comprises Betamethasone Dipropionate Cream or Ointment, Clobetasol Propionate Cream or Ointment, Desoximetasone Cream or Ointment, Fluocinonide Cream or Ointment, Halobetasol Propionate Cream, Triamcinolone Acetonide Cream or Ointment, or a combination thereof.

In one embodiment, the contents of the compounded capsule and the corticosteroid cream or ointment are combined in amounts sufficient to formulate the topical composition comprising between approximately 10% and approximately 25% urea by weight and between approximately 0.025% and approximately 0.098% high potency corticosteroid by weight. The corticosteroid cream or ointment may be a Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, or a combination thereof. In one example, the corticosteroid cream or ointment comprises Clobetasol Propionate Cream or Ointment, Fluocinonide Cream or Ointment, Halobetasol Propionate Cream, or Desoximetasone Cream or Ointment, or a combination thereof. According to one example, the corticosteroid cream or ointment comprises Fluocinonide Cream, 0.1%. The Fluocinonide Cream, 0.1%, may be combined in an amount wherein the topical composition comprises between approximately 0.05% and approximately 0.088% of the high potency corticosteroid fluocinonide by weight. The contents of the compounded capsule may be combined in an amount wherein the topical composition comprises approximately 10% to approximately 30% urea by weight. According to another example, the corticosteroid cream or ointment comprises Halobetasol Cream, 0.05%, or Betamethasone Dipropionate Cream, 0.05%. The Halobetasol Cream, 0.05%, or Betamethasone Dipropionate Cream, 0.05%, may be combined in an amount wherein the topical composition comprises between approximately 0.035% and approximately 0.050% of the high potency corticosteroid halobetasol or betamethasone by weight. The contents of the compounded capsule may be combined in an amount wherein the topical composition comprises approximately 10% to approximately 25% urea by weight. In another example, the corticosteroid cream or ointment comprises Clobetasol Propionate Cream, 0.05%. The Clobetasol Propionate Cream, 0.05%, may be combined in an amount wherein the topical composition comprises between approximately 0.035% and approximately 0.050% of the high potency corticosteroid clobetasol by weight. The contents of the compounded capsule may be combined in an amount wherein the topical composition comprises approximately 10% to approximately 25% urea by weight. In another example, the corticosteroid cream or ointment comprises Triamcinolone Acetonide Cream, 0.1%. The Triamcinolone Acetonide Cream, 0.1%, may be combined in an amount wherein the topical composition comprises between approximately 0.06% and approximately 0.09% of the high potency corticosteroid triamcinolone by weight. The contents of the compounded capsule may be combined in an amount wherein the topical composition comprises approximately 10% to approximately 25% urea by weight.

In another aspect, a method of treating a hyperkeratotic skin condition includes combining contents of a compounded capsule with corticosteroid cream or ointment that includes a high potency corticosteroid to formulate a topical composition for application to a skin area affected by hyperkeratosis. The contents of the capsule may include urea powder, and the corticosteroid cream or ointment may include Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, or a combination thereof.

In various embodiments, the corticosteroid cream or ointment comprises Fluocinonide Cream, 0.1% or Triamcinolone Acetonide Cream, 0.1%, combined in an amount wherein the topical composition comprises between approximately 0.05% and approximately 0.088% of the high potency corticosteroid fluocinonide or triamcinolone by weight. The contents of the compounded capsule may be combined in an amount wherein the topical composition comprises approximately 10% to approximately 30% urea by weight. In another embodiment, the corticosteroid cream or ointment comprises Clobetasol Propionate Cream, 0.05%, Betamethasone Dipropionate Cream, 0.05%, or Halobetasol Propionate Cream, 0.05% combined in an amount wherein the topical composition comprises between approximately 0.035% and approximately 0.050% of the high potency corticosteroid clobetasol, betamethasone, or halobetasol by weight. The contents of the compounded capsule may be combined in an amount wherein the topical composition comprises approximately 10% to approximately 25% urea by weight.

In another aspect, a method of treating a hyperkeratotic skin condition includes dispensing a kit for treatment of a hyperkeratotic skin condition. The kit may include a compounded capsule containing urea powder and a corticosteroid cream or lotion comprising a high potency corticosteroid. Execution of the kit may include combining the urea powder contents of the compounded capsule with the corticosteroid cream or ointment comprising the high potency corticosteroid to formulate a topical composition for application to a skin area affected by the hyperkeratotic skin condition. The corticosteroid cream or ointment may be Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Halobetasol Propionate Cream or Ointment, Mometasone Furoate Cream or Ointment, Flurandrenolide Cream or Ointment, or a combination thereof.

In one embodiment, the corticosteroid cream or ointment comprises Fluocinonide Cream, 0.1%. The Fluocinonide Cream, 0.1%, and compounded capsule may be dispensed with the kit in amounts wherein combining the urea powder contents of the compounded capsule with the Fluocinonide Cream, 0.1%, formulates the topical composition comprising between approximately 0.05% and approximately 0.088% of the high potency corticosteroid fluocinonide by weight and approximately 10% to approximately 30% urea by weight.

In another embodiment, the corticosteroid cream or ointment comprises Halobetasol Cream, 0.05%. The Halobetasol Cream, 0.05%, and compounded capsule may be dispensed with the kit in amounts wherein combining the urea powder contents of the compounded capsule with the Halobetasol Cream, 0.05%, formulates the topical composition comprising between approximately 0.0350% and approximately 0.0500% of the high potency corticosteroid halobetasol by weight and approximately 10% to approximately 35% urea by weight.

DESCRIPTION

The present disclosure describes topical compositions. The topical compositions may include urea and a corticosteroid. In various embodiments, the topical compositions may comprise a compounded topical composition for treatment of a hyperkeratotic condition that includes urea and a corticosteroid. Some embodiments include a kit for treating a hyperkeratotic skin condition including a capsule containing urea powder and a commercially available corticosteroid cream that may be compounded proximate to the time of administration by a patient, caregiver, or medical professional.

In various embodiments, a method of treating a hyperkeratotic skin condition comprises administering the compounded topical composition to the affected skin. The administration may include application of the compounded composition to the affected skin one or more times a day, such as twice, three times, or four times a day.

The hyperkeratotic skin condition treated may be chronic eczema, corns, calluses, warts, seborrheic keratosis, lichen planus, actinic keratosis, as examples. The hyperkeratotic skin conditions may be caused by irritation, such as physical pressure or rubbing, chemical, infection, sunlight or radiation, or inherited conditions, for example.

The compounded topical composition may be any type of composition. For example, the topical composition may be or include a lotion, gel, ointment, foam, cream, emulsion, or any other composition intended for application to the skin of a patient.

As introduced above, the compounded topical composition may include urea and a corticosteroid. Urea has physiologic importance as a nitrogen carrier and osmolyte. Urea is produced biologically within the urea cycle as nitrogenous compounds or amino acids are metabolized. Industrial production of urea involves conversion of ammonia and carbon dioxide to urea. Urea is a compound formed in the liver from ammonia produced by the deamination of amino acids. In various embodiments, urea may be provided in a commercial ointment or cream. In some embodiments, urea may be provided in a powder, such as a bulk urea powder. Other embodiments may incorporated other urea formats, such as urea solutions. The urea may be pure or substantially pure and obtained from a bulk source. In one example, urea can be urea powder USP 99.6. The urea may be provided in a capsule, separate for the corticosteroid, for ease of compounding proximate to administration. For example, a kit for treating a hyperkeratotic skin condition may include a capsule containing urea powder and a commercially available corticosteroid cream. A patient or caregiver may open the capsule and combine the urea with the corticosteroid cream prior to administration. The corticosteroid cream may be a cream, ointment, foam, emulsion, lotion, for example. In one embodiment, urea can be a commercially available urea cream, such as REA LO 40®, which is a 40.0% urea cream. Each gram of REA LO 40® contains 400 mg urea as the active ingredient and the following inactive ingredients: purified water, emulsifying wax, glycerin, isopropyl myristate, sorbitol, neopentyl glycol dicaprylate/dicaprate, tridecyl stearate, tridecyl trimellitate and dimethyl isosorbide.

The compounded topical composition may include any amount of urea by weight. In various embodiments, the amount of urea by weight in the compounded topical composition may be between approximately 10% and approximately 25%, between approximately 15% and approximately 25%, between approximately 20% and approximately 25%, between approximately 10% and approximately 20%, between approximately 10% and approximately 15%, or between approximately 5% and approximately 30%. In these or other embodiments, the amount of urea by weight in the topical composition may be approximately 10%, approximately 11%, approximately 12%, approximately 14%, approximately 15%, approximately 16%, approximately 18%, approximately 20%, approximately 22%, approximately 24%, approximately 25%, or any other percentage (including any percentage between approximately 5% and approximately 30% or between approximately 25% and approximately 50%, for example).

In various embodiments, the urea may be included in the topical composition in the form of a commercially available urea cream. For example, a component of the topical composition may be a commercial urea cream providing all or a portion of the urea in the topical composition. The urea cream may comprise various percentages of urea by weight (prior to compounding or prior to combination with another cream), such as 10%, 15%, 20%, 25%, 30%, 35%, 40%, or any other commercially available percentage by weight.

In various embodiments, the urea cream may be Urix 40 Urea Cream marketed by Topix Pharmaceuticals, Inc. Urix 40 Urea Cream includes 40% urea or 400 mg urea per gram and further includes Carbomer, Cyclomethicone, Dimethicone Silyate, Dimethiconol, Glycerin, Hydrogenated Lecithin, Imidazolidinyl Urea, Petrolatum, Phenyl Trimethicone, Polyphosphorylcholine Glycol Acrilate, Triethanolamine, Water, and Xanthan Gum. In additional embodiments, the urea cream may be Rea Lo 40 topical or Rea Lo 30 topical marketed by Crown Laboratories. Rea Lo 40 topical comprises 400 mg urea per gram and Rea Lo 30 topical comprises 300 mg urea per gram. Rea Lo 40 topical and Rea Lo 30 topical further include purified water, emulsifying wax, glycerin, isopropyl myristate, sorbitol, neopentyl, glycol dicaprylate/dicaprate, tridecyl stearate, tridecyl trimellitate and dimethyl isosorbide. In additional embodiments, the urea cream may be Urea 10% Cream by Stratus Pharmaceuticals, Inc. Urea 10% Cream includes 10% urea or 100 mg urea per gram, and further includes Carbomer, Fragrance, Isopropyl Myristate, Isopropyl Palmitate, Propylene Glycol, Purified Water, Sodium Laureth Sulfate, Stearic Acid, Trolamine and Xanthan Gum.

It is to be understood that the above urea creams (or any other urea cream) may be diluted or cut prior to or, in some embodiments, after compounding or otherwise combining the urea cream with additional creams and/or actives. Thus, the topical composition may comprise less urea by weight than was present in the urea cream prior to compounding or combination with another cream and/or active.

In various embodiments, the urea may be included in the topical composition in the form of a compounded urea topical. For example, urea may be added to a base (such as a commercially available base) in order to form a compounded urea topical. The base may be a foam, cream, gel, lotion, ointment, or emulsion (oil-in-water or water-in-oil), for example, suitable for topical application, e.g., to skin or nails. For brevity, such bases may be referred to as cream bases or base creams herein. Unless otherwise specified, a cream base or a base cream as used herein may include bases that are foams, gels, lotions, ointments, creams, or emulsions (oil-in-water or water-in-oil).

In some embodiments, the cream base includes polyethylene glycol (PEG). In other embodiments, the cream base is PEG-free. In these or other embodiments, the cream base may include a silicon or silicon variant. In some embodiments, the cream base is silicon-free. An example cream base comprising a foam may include a propellant such as butane. Cream bases comprising a foam may also comprise additional characteristics such as that of an emulsion, such as an oil-in-water emulsion. In one example, the cream base comprises an ointment, e.g., water soluble/miscible, absorption, water-in-oil emulsion, or oil-in-water emulsion. Example cream bases comprising ointments may include hydrophilic petrolatum, white tetrolatum, hydrophilic ointment, white ointment, anhydrous lanolin, hydrous lanolin, PEG ointment, or combinations thereof.

The cream base may comprise various emollients. For example, in one embodiment the cream base comprises a keratolytic emollient. In one embodiment, the cream base may comprise one or more of acrylates copolymer, alcohol, camphor, carbomer, dimethyl isosorbide, disodium EDTA, dl-alphatocopheryl acetate, edetate disodium, emulsifying wax, *eucalyptus* oil, flavonoids, glycerin, glycol dicaprylate/ dicaprate, hydroxyethyl cellulose, isopropyl myristate, lactic acid, meadowsweet extract, menthol, mineral oil, neopentyl, phenolic glycosides, polyethylene glycol (PEG), polysorbate 85, purified water, titanium dioxide, tridecyl stearate, tridecyl trimellitate, sodium hydroxide, sodium hydroxide, sorbitol, stearic acid, or zinc pyrithione. In various embodiments, the cream base may be a commercially available topical base. For example, in some embodiments, the cream base may be the topical base Spira-Wash™ Gel or Lipoderm® both marketed by Professional Compounding Centers of America (PCCA), Houston, Tex.

The urea may be added to the base in any manner to form the compounded urea cream. As an example, the urea may be mixed into the base. Also, any amount of the urea may be added to the base to form the compounded urea cream. For example, an amount of urea may be added to the base so as to cause the compounded urea cream to include various percentages of urea by weight (prior to combination with another cream) such as 10%, 15%, 20%, 25%, 30%, 35%, 40%, or any other percentage.

The corticosteroid is preferably a high potency corticosteroid. In various embodiments, the compounded topical composition comprises urea and a high potency corticosteroid selected from amcinonide, betamethasone, clobetasol, desoximetasone, diflorasone, flurandrenolide, fluticasone, fluocinonide, halcinonide, halobetasol, mometasone, triamcinolone, or combinations thereof. The corticosteroids identified above may include pharmaceutically acceptable salts and derivatives. In one example, the compounded topical composition comprises urea and a high potency corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof. In another example, the compounded topical composition comprises urea and a high potency corticosteroid selected from amcinonide, betamethasone dipropionate, clobetasol propionate, desoximetasone, diflorasone diacetate, flurandrenolide, fluocinonide, halcinonide, halobetasol propionate, mometasone furoate. In yet another example, the compounded topical composition comprises urea and a high potency corticosteroid selected from clobetasol, desoximetasone, fluocinonide, halobetasol, or combinations thereof, including clobetasol propionate or halobetasol propionate.

In various embodiments, the compounded topical composition comprises between approximately 2.5% and approximately 50% urea by weight and between approximately 0.001% and approximately 0.5% of the selected high potency corticosteroid by weight, which in some embodiments may include multiple high potency corticosteroids in combination, such as between approximately 2.5% and approximately 25% urea by weight and between approximately 0.025% and approximately 0.100% high potency corticosteroid by weight, between approximately 10% and approximately 35% urea by weight and between approximately 0.025% and approximately 0.100% high potency corticosteroid by weight, between approximately 15% and approximately 25% urea by weight and between approximately 0.025% and approximately 0.100% high potency corticosteroid by weight, between approximately 25% and approximately 40% urea by weight and between approximately 0.025% and approximately 0.100% high potency corticosteroid by weight, between approximately 30% and approximately 50% urea by weight and between approximately 0.025% and approximately 0.100% high potency corticosteroid by weight, between approximately 2.5% and approximately 25% urea by weight and between approximately 0.05% and approximately 0.1% high potency corticosteroid by weight, between approximately 10% and approximately 35% urea by weight and between approximately 0.05% and approximately 0.1% high potency corticosteroid by weight, between approximately 15% and approximately 25% urea by weight and between approximately 0.05% and approximately 0.1% high potency corticosteroid by weight, between approximately 25% and approximately 40% urea by weight and between approximately 0.05% and approximately 0.1% high potency corticosteroid by weight, between approximately 30% and approximately 50% urea by weight and between approximately 0.05% and approximately 0.1% high potency corticosteroid by weight, between approximately 2.5% and approximately 25% urea by weight and between approximately 0.03% and approximately 0.05% high potency corticosteroid by weight, between approximately 10% and approximately 35% urea by weight and between approximately 0.03% and approximately 0.05% high potency corticosteroid by weight, between approximately 15% and approximately 25% urea by weight and between approximately 0.03% and approximately 0.05% high potency corticosteroid by weight, between approximately 25% and approximately 40% urea by weight and between approximately 0.03% and approximately 0.05% high potency corticosteroid by weight, between approximately 30% and approximately 50% urea by weight and between approximately 0.03% and approximately 0.05% high potency corticosteroid by weight, between approximately 2.5% and approximately 25% urea by weight and between approximately 0.05% and approximately 0.085% high potency corticosteroid by weight, between approximately 10% and approximately 35% urea by weight and between approximately 0.05% and approximately 0.085% high potency corticosteroid by weight, between approximately 15% and approximately 25% urea by weight and between approximately 0.05% and approximately 0.085% high potency corticosteroid by weight, between approximately 25% and approximately 40% urea by weight and between approximately 0.05% and approximately 0.085% high potency corticosteroid by weight, between approximately 30% and approximately 50% urea by weight and between approximately 0.05% and approximately 0.085% high potency corticosteroid by weight.

In various embodiments, the compounded topical composition comprises between 5% and 50% urea, such as approximately 7%, approximately 9%, approximately 11%, approximately 13%, approximately 14%, approximately 15%, approximately 16%, approximately 17%, approximately 19%, approximately 20%, approximately 21%, approximately 22%, approximately 23%, approximately 24%, approximately 25%, approximately 27%, approximately 29%, approximately 31%, approximately 35%, approximately 39%, approximately 43%, approximately 47%, approximately 50%, less than approximately 40%, less than approximately 30%, less than approximately 25%, less than approximately 20%, or less than approximately 15%. In any of the embodiments above or elsewhere herein, the compounded topical composition may comprise between approximately 0.001% and approximately 0.5% of the selected high potency corticosteroid by weight, which in some embodiments may include multiple high potency corticosteroids in combination, such as approximately 0.005%, approximately 0.01%, approximately 0.02%, approximately 0.03%, approximately 0.04%, approximately 0.045%, approximately 0.05%, approximately 0.055%, approximately 0.06%, approximately 0.065%, approximately 0.07%, approximately 0.075%, approximately 0.08%, approximately 0.085%, approximately 0.09%, approximately 0.095%, approximately 0.1%, approximately 0.2%, approximately 0.3%, approximately 0.4%, approximately 0.5%, less than approximately 0.2%, less than approximately 0.1%, less than approximately 0.09%, less than approximately 0.08%, less than approximately 0.07%, less than approximately 0.06%, less than approximately 0.05%, less than approximately 0.04%, less than approximately 0.03%, less than approximately 0.02%, or less than approximately 0.01%.

In various embodiments, the compounded topical composition comprises urea and the high-potency corticosteroid compounded within a topical base, which may be a topical base cream, ointment, gel, emulsion (o/w, w/o), foam, spray. In some embodiments, a commercially available a topical medication composition may be utilized as a topical base for compounding the topical composition. Corticosteroid may be compounded with the topical base, which may be a topical medication composition, in a powder form, which in some embodiments, may include ground oral tablets of the corticosteroid. In some embodiments, corticosteroid solutions, such as corticosteroid solutions for injection or oral administration may be compounded with the topical base, which may be a commercial topical medication composition. Thus, is some embodiments a corticosteroid comprising a bulk powder or a medication composition format such as a commercial tablet or solution for injection or oral administration may be compounded with a topical base, which may include a topical medication composition comprising another active agent medication such as an antifungal, antibiotic, another corticosteroid, an NSAID, antidepressant, anticonvulsant, opioid, local anesthetic, analgesic, anti-inflammatory, or combinations thereof.

The urea and the high potency corticosteroid may be included in the compounded topical composition in any form. In various embodiments, the urea may be included in the compounded topical composition in the form of a commercially available urea topical composition, and the high potency corticosteroid may be included in the topical composition in the form of a commercially available corticosteroid topical composition. In various embodiments, the urea may be included in the topical composition in the form of a compounded urea cream, and the high potency corticosteroid may be included in the topical composition in the form of a compounded corticosteroid cream or ointment. In various embodiments, the urea may be included in the compounded topical composition in the form of a commercially available urea cream, and the high potency corticosteroid may be included in the compounded topical composition in the form of a compounded high potency corticosteroid cream or ointment. In various embodiments, the urea may be included in the compounded topical composition in the form of a compounded urea cream, and the high potency corticosteroid may be included in the topical composition in the form of a commercially available high potency corticosteroid cream or ointment.

In some embodiments, the high potency corticosteroid is provided in a topical medication comprising a commercially manufactured, commercially available topical corticosteroid composition, which may include creams, ointments, gels, emulsions (o/w, w/o), foams, sprays/solutions. The urea may be compounded with the topical corticosteroid as a powder, solution, or commercially available or compounded topical urea composition as described above and elsewhere herein.

In an embodiment, the compounded topical composition comprises urea powder, solution, or commercially available or compounded topical urea composition, as described above and elsewhere herein, compounded with a commercially available topical corticosteroid composition comprising amcinonide, which may include creams, ointments, gels, emulsions (o/w, w/o), foams, sprays/solutions.

In one example the topical corticosteroid composition comprising amcinonide comprises amcinonide topical corticosteroid cream. Amcinonide cream is available as Amcinonide Cream USP, 0.1%, wherein each gram contains 1 mg of active steroid Amcinonide, Benzyl Alcohol 2% (wt/wt) as preservative, Emulsifying Wax, Glycerin, Isopropyl Palmitate, Lactic Acid, Purified Water and Sorbitol Solution. Additional commercially available strengths and formulations may be used according to the present disclosure.

In another example the topical corticosteroid composition comprising amcinonide comprises amcinonide ointment. Amcinonide ointment is available as Amcinonide Ointment USP, 0.1%, wherein each gram contains 1 mg of the active steroid amcinonide in a specially formulated base composed of Benzyl Alcohol 2%, (wt/wt) as preservative, White Petrolatum, USP, Emulsifying Wax, and Antioxidant Blend (Propylene Glycol, Butylated Hydroxyanisole, Propyl Gallate and Citric Acid). Additional commercially available strengths and formulations may be used according to the present disclosure.

In another example the topical corticosteroid composition comprising amcinonide comprises amcinonide lotion. Amcinonide lotion is available as Amcinonide Lotion, 0.1%, wherein each gram contains 1 mg of the active steroid amcinonide in a white, smooth, homogeneous, opaque emulsion composed of Benzyl Alcohol 1% (wt/wt) as preservative, Emulsifying Wax, Glycerin, Isopropyl Palmitate, Purified Water, Sorbitol Solution and Polyethylene Glycol 400. Dilute Lactic Acid is used for pH adjustment, if required. Additional commercially available strengths and formulations may be used according to the present disclosure.

In various embodiments, the compounded topical composition comprises between approximately 2.5% and approximately 50% urea by weight and between approximately 0.05% and approximately 0.098% amcinonide by weight, such as between approximately 2.5% and approximately 25% urea by weight and between approximately 0.075% and approximately 0.098% amcinonide by weight, between approximately 0.05% and approximately 0.075% amcinonide by weight, between approximately 0.065% and approximately 0.085% amcinonide by weight, or between approximately 0.06% and approximately 0.07% amcinonide by weight; between approximately 10% and approximately 35% urea by weight and between approximately 0.075% and approximately 0.098% amcinonide by weight, between approximately 0.05% and approximately 0.075% amcinonide by weight, between approximately 0.065% and approximately 0.085% amcinonide by weight, or between approximately 0.06% and approximately 0.07% amcinonide by weight; between approximately 15% and approximately 25% urea by weight and between approximately 0.075% and approximately 0.098% amcinonide by weight, between approximately 0.05% and approximately 0.075% amcinonide by weight, between approximately 0.065% and approximately 0.085% amcinonide by weight, or between approximately 0.06% and approximately 0.07% amcinonide by weight; between approximately 25% and approximately 40% urea by weight and between approximately 0.075% and approximately 0.098% amcinonide by weight, between approximately 0.05% and approximately 0.075% amcinonide by weight, between approximately 0.065% and approximately 0.085% amcinonide by weight, or between approximately 0.06% and approximately 0.07% amcinonide by weight; or between approximately 30% and approximately 50% urea by weight and between approximately 0.075% and approximately 0.098% amcinonide by weight, between approximately 0.05% and approximately 0.075% amcinonide by weight, between approximately 0.065% and approximately 0.085% amcinonide by weight, or between approximately 0.06% and approximately 0.07% amcinonide by weight.

In various embodiments, the compounded composition is provided in a kit for treating a hyperkeratotic skin condition including a capsule containing urea powder and a commercially available corticosteroid topical composition comprising amcinonide, e.g., cream, ointment, or lotion, that may be compounded proximate to the time of administration by a patient, caregiver, or medical professional. In one example, the kit includes a capsule comprising a suitable amount of urea powder to mix with the topical amcinonide composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 20% urea and 0.08% amcinonide. According to one example, the kit includes a dosage unit for formulating the compounded composition comprising a capsule containing 500 mg urea powder and 2 g of a 0.1% topical amcinonide composition, e.g., Amcinonide Cream USP, 0.1%, Amcinonide Ointment USP, 0.1%, or Amcinonide Lotion USP, 0.1%. The topical amcinonide composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical amcinonide composition, e.g., Amcinonide Cream USP, 0.1%, Amcinonide Ointment USP, 0.1%, or Amcinonide Lotion USP, 0.1%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising betamethasone, such as betamethasone dipropionate, which may include creams, ointments, gels, emulsions (o/w, w/o), foams, sprays/solutions.

In one example the topical corticosteroid composition comprising betamethasone comprises betamethasone dipropionate cream. Betamethasone dipropionate cream is available as Betamethasone Dipropionate Cream, 0.05%, wherein each gram contains 0.64 mg betamethasone dipropionate USP (equivalent to 0.5 mg betamethasone) in a hydrophilic cream base of purified water, mineral oil, white petrolatum, polyethylene glycol 1000 monocetyl ether, cetostearyl alcohol, monobasic sodium phosphate, propylene glycol, phosphoric acid and/or sodium hydroxide for pH adjustment and chlorocresol as a preservative. Additional commercially available strengths and formulations may be used according to the present disclosure.

In one example the topical corticosteroid composition comprising betamethasone comprises betamethasone dipropionate ointment. Betamethasone dipropionate ointment is available as Betamethasone Dipropionate Ointment USP, 0.05%, wherein each gram contains 0.643 mg betamethasone dipropionate USP (equivalent to 0.5 mg betamethasone), in a white ointment base of propylene glycol; propylene glycol stearate; white petrolatum; and white wax. Additional commercially available strengths and formulations may be used according to the present disclosure.

In one example the topical corticosteroid composition comprising betamethasone comprises betamethasone dipropionate lotion. Betamethasone dipropionate lotion is available as Betamethasone Dipropionate Lotion USP, 0.05%, wherein each gram contains 0.64 mg betamethasone dipropionate (equivalent to 0.5 mg betamethasone) in a vehicle of isopropyl alcohol and purified water slightly thickened with carbomer 974P. Sodium hydroxide solution to adjust pH, if required. Additional commercially available strengths and formulations may be used according to the present disclosure.

In one example the topical corticosteroid composition comprising betamethasone comprises betamethasone dipropionate gel. Betamethasone dipropionate gel is available as Betamethasone Dipropionate Gel USP, 0.05%, wherein each gram contains 0.64 mg betamethasone dipropionate, USP (equivalent to 0.5 mg betamethasone), in an augmented gel base of purified water, propylene glycol, carbomer 940, and sodium hydroxide. Additional commercially available strengths and formulations may be used according to the present disclosure.

In various embodiments, the compounded topical composition comprises between approximately 2.5% and approximately 50% urea by weight and between approximately 0.025% and approximately 0.0488% betamethasone by weight, such as between approximately 2.5% and approximately 25% urea by weight and between approximately 0.0350% and approximately 0.0488% betamethasone by weight, between approximately 0.0250% and approximately 0.0375% betamethasone by weight, between approximately 0.0325% and approximately 0.0425% betamethasone by weight, or between approximately 0.0275% and approximately 0.0350% betamethasone by weight; between approximately 10% and approximately 35% urea by weight and between approximately 0.0350% and approximately 0.0488% betamethasone by weight, between approximately 0.0250% and approximately 0.0375% betamethasone by weight, between approximately 0.0325% and approximately 0.0425% betamethasone by weight, or between approximately 0.0275% and approximately 0.0350% betamethasone by weight; between approximately 15% and approximately 25% urea by weight and between approximately 0.0350% and approximately 0.0488% betamethasone by weight, between approximately 0.0250% and approximately 0.0375% betamethasone by weight, between approximately 0.0325% and approximately 0.0425% betamethasone by weight, or between approximately 0.0275% and approximately 0.0350% betamethasone by weight; between approximately 25% and approximately 40% urea by weight and between approximately 0.0350% and approximately 0.0488% betamethasone by weight, between approximately 0.0250% and approximately 0.0375% betamethasone by weight, between approximately 0.0325% and approximately 0.0425% betamethasone by weight, or between approximately 0.0275% and approximately 0.0350% betamethasone by weight; or between approximately 30% and approximately 50% urea by weight and between approximately 0.0350% and approximately 0.0488% betamethasone by weight, between approximately 0.0250% and approximately 0.0375% betamethasone by weight, between approximately 0.0325% and approximately 0.0425% betamethasone by weight, or between approximately 0.0275% and approximately 0.0350% betamethasone by weight.

In various embodiments, the compounded composition is provided in a kit for treating a hyperkeratotic skin condition including a capsule containing urea powder and a commercially available corticosteroid topical composition comprising betamethasone, e.g., betamethasone dipropionate cream, ointment, lotion, or gel, that may be compounded proximate to the time of administration by a patient, caregiver, or medical professional. In one example, the kit includes a capsule comprising a suitable amount of urea powder to mix with the topical betamethasone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% betamethasone. According to one example, the kit includes a dosage unit for formulating the compounded composition comprising a capsule containing 500 mg urea powder and 2.5 g of a 0.05% topical betamethasone composition, e.g., Betamethasone Dipropionate Cream USP, 0.05%, Betamethasone Dipropionate Ointment USP, 0.05%, Betamethasone Dipropionate Lotion USP, 0.05%, or Betamethasone Dipropionate Gel USP, 0.05%. The topical betamethasone composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical betamethasone composition, e.g., Betamethasone Dipropionate Cream USP, 0.05%, Betamethasone Dipropionate Ointment USP, 0.05%, Betamethasone Dipropionate Lotion USP, 0.05%, or Betamethasone Dipropionate Gel USP, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

As introduced above, in an embodiment, the compounded topical composition comprises urea powder, solution, or topical urea composition compounded with a topical corticosteroid composition comprising betamethasone valerate, which may include creams, ointments, gels, emulsions (o/w, w/o), foams, sprays/solutions.

In one example the topical corticosteroid composition comprising betamethasone comprises a betamethasone valerate cream. Betamethasone valerate cream is available as Betamethasone Valerate Cream, 0.1%, wherein each gram contains 1.2 mg betamethasone valerate (equivalent to 1 mg betamethasone) in a soft, white, hydrophilic cream of purified water, mineral oil, sodium phosphate monobasic (monohydrate), white petrolatum, polyethylene glycol 1000, ceteareth-15, stearyl alcohol, cetyl alcohol, propylene glycol, phosphoric acid (to adjust pH, if required); chlorocresol is present as a preservative. Additional commercially available strengths and formulations may be used according to the present disclosure.

In one example the topical corticosteroid composition comprising betamethasone comprises betamethasone dipropionate valerate ointment. Betamethasone valerate ointment is available as Betamethasone Valerate Ointment, 0.1%, wherein each gram contains 1.2 mg betamethasone valerate (equivalent to 1 mg betamethasone) in an ointment base of white petrolatum, mineral oil, and hydrogenated lanolin. Additional commercially available strengths and formulations may be used according to the present disclosure.

In one example the topical corticosteroid composition comprising betamethasone comprises betamethasone dipropionate valerate lotion. Betamethasone valerate lotion is available as Betamethasone Valerate Lotion, 0.1%, wherein each gram contains 1.2 mg betamethasone valerate (equivalent to 1 mg betamethasone) in a vehicle of isopropyl alcohol and water slightly thickened with carbomer 934P. Sodium hydroxide is used to adjust pH. Additional commercially available strengths and formulations may be used according to the present disclosure.

In various embodiments, the compounded topical composition comprises between approximately 2.5% and approximately 50% urea by weight and between approximately 0.05% and approximately 0.098% betamethasone by weight, such as between approximately 2.5% and approximately 25% urea by weight and between approximately 0.075% and approximately 0.098% betamethasone by weight, between approximately 0.05% and approximately 0.075% betamethasone by weight, between approximately 0.065% and approximately 0.085% betamethasone by weight, or between approximately 0.06% and approximately 0.07% betamethasone by weight; between approximately 10% and approximately 35% urea by weight and between approximately 0.075% and approximately 0.098% betamethasone by weight, between approximately 0.05% and approximately 0.075% betamethasone by weight, between approximately 0.065% and approximately 0.085% betamethasone by weight, or between approximately 0.06% and approximately 0.07% betamethasone by weight; between approximately 15% and approximately 25% urea by weight and between approximately 0.075% and approximately 0.098% betamethasone by weight, between approximately 0.05% and approximately 0.075% betamethasone by weight, between approximately 0.065% and approximately 0.085% betamethasone by weight, or between approximately 0.06% and approximately 0.07% betamethasone by weight; between approximately 25% and approximately 40% urea by weight and between approximately 0.075% and approximately 0.098% betamethasone by weight, between approximately 0.05% and approximately 0.075% betamethasone by weight, between approximately 0.065% and approximately 0.085% betamethasone by weight, or between approximately 0.06% and approximately 0.07% betamethasone by weight; or between approximately 30% and approximately 50% urea by weight and between approximately 0.075% and approximately 0.098% betamethasone by weight, between approximately 0.05% and approximately 0.075% betamethasone by weight, between approximately 0.065% and approximately 0.085% betamethasone by weight, or between approximately 0.06% and approximately 0.07% betamethasone by weight.

In various embodiments, the compounded composition is provided in a kit for treating a hyperkeratotic skin condition including a capsule containing urea powder and a commercially available corticosteroid topical composition comprising betamethasone, e.g., betamethasone valerate cream, ointment, or lotion, that may be compounded proximate to the time of administration by a patient, caregiver, or medical professional. In one example, the kit includes a capsule comprising a suitable amount of urea powder to mix with the topical betamethasone valerate composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 20% urea and 0.08% betamethasone. According to one example, the kit includes a dosage unit for formulating the compounded composition comprising a capsule containing 500 mg urea powder and 2 g of a 0.1% topical betamethasone valerate composition, e.g., Betamethasone Valerate Cream, 0.1%, Betamethasone Valerate Ointment, 0.1%, or Betamethasone Valerate Lotion, 0.1%. The topical betamethasone valerate composition may be packaged in specific dosage weights or may be provided in multi-dose packaging, e.g., 160 g, 150 g, 120 g, 100 g, 60 g, 30 g, 15 g tubes. In one embodiment, the kit may include urea cream and a topical betamethasone composition, e.g., Betamethasone Valerate Cream, 0.1%, Betamethasone Valerate Ointment, 0.1%, or Betamethasone Valerate Lotion, 0.1%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising clobetasol, which may include creams, ointments, gels, emulsions (o/w, w/o), foams, sprays/solutions.

In one example the topical corticosteroid composition comprising clobetasol comprises clobetasol propionate cream. Clobetasol propionate cream is available as Clobetasol Propionate Cream, 0.05%, wherein each gram contains clobetasol propionate 0.5 mg in a cream base composed of cetyl alcohol, citric acid, glycol stearate, lanolin oil, methylparaben, PEG-8 stearate, polysorbate 60, propylene glycol, propylparaben, purified water, sodium citrate, stearyl alcohol, and white petrolatum. Sodium hydroxide may be used to adjust pH. Clobetasol propionate cream is also available as Clobetasol Propionate Emollient Cream, 0.05%, containing clobetasol propionate 0.5 mg/g in an emollient base of cetomacrogol 1000, cetostearyl alcohol, citric acid, dimethicone 360, imidurea as a preservative, isopropyl myristate, propylene glycol, purified water, and sodium citrate. Additional commercially available strengths and formulations may be used according to the present disclosure.

In one example the topical corticosteroid composition comprising clobetasol comprises clobetasol propionate ointment. Clobetasol propionate ointment is available as Clobetasol Propionate Ointment, 0.05%, wherein each gram contains clobetasol propionate 0.5 mg in an ointment base composed of propylene glycol, sorbitan sesquioleate, and white petrolatum. Additional commercially available strengths and formulations may be used according to the present disclosure.

In one example the topical corticosteroid composition comprising clobetasol comprises clobetasol propionate foam. Clobetasol propionate foam is available as Clobetasol Propionate Foam, 0.05%, (Emulsion) wherein each gram contains 0.5 mg clobetasol propionate, USP. The foam also contains anhydrous citric acid, cetyl alcohol, cyclomethicone, glycerin, isopropyl myristate, polyoxyl 20 cetostearyl ether, potassium citrate monohydrate, propylene glycol, purified water, sorbitan monolaurate, and phenoxyethanol as a preservative. Additional commercially available strengths and formulations may be used according to the present disclosure.

In one example the topical corticosteroid composition comprising clobetasol comprises clobetasol propionate gel. Clobetasol propionate gel is available as Clobetasol Propionate Gel, 0.05%, wherein each gram contains 0.5 mg clobetasol propionate in a base of propylene glycol, carbomer 934P, sodium hydroxide and purified water. Additional commercially available strengths and formulations may be used according to the present disclosure.

In various embodiments, the compounded topical composition comprises between approximately 2.5% and approximately 50% urea by weight and between approximately 0.025% and approximately 0.0488% clobetasol by weight, such as between approximately 2.5% and approximately 25% urea by weight and between approximately 0.0350% and approximately 0.0488% clobetasol by weight, between approximately 0.0250% and approximately 0.0375% clobetasol by weight, between approximately 0.0325% and approximately 0.0425% clobetasol by weight, or between approximately 0.0275% and approximately 0.0350% clobetasol by weight; between approximately 10% and approximately 35% urea by weight and between approximately 0.0350% and approximately 0.0488% clobetasol by weight, between approximately 0.0250% and approximately 0.0375% clobetasol by weight, between approximately 0.0325% and approximately 0.0425% clobetasol by weight, or between approximately 0.0275% and approximately 0.0350% clobetasol by weight; between approximately 15% and approximately 25% urea by weight and between approximately 0.0350% and approximately 0.0488% clobetasol by weight, between approximately 0.0250% and approximately 0.0375% clobetasol by weight, between approximately 0.0325% and approximately 0.0425% clobetasol by weight, or between approximately 0.0275% and approximately 0.0350% clobetasol by weight; between approximately 25% and approximately 40% urea by weight and between approximately 0.0350% and approximately 0.0488% clobetasol by weight, between approximately 0.0250% and approximately 0.0375% clobetasol by weight, between approximately 0.0325% and approximately 0.0425% clobetasol by weight, or between approximately 0.0275% and approximately 0.0350% clobetasol by weight; or between approximately 30% and approximately 50% urea by weight and between approximately 0.0350% and approximately 0.0488% clobetasol by weight, between approximately 0.0250% and approximately 0.0375% clobetasol by weight, between approximately 0.0325% and approximately 0.0425% clobetasol by weight, or between approximately 0.0275% and approximately 0.0350% clobetasol by weight.

In various embodiments, the compounded composition is provided in a kit for treating a hyperkeratotic skin condition including a capsule containing urea powder and a commercially available corticosteroid topical composition comprising clobetasol, e.g., clobetasol cream, ointment, foam, or gel, that may be compounded proximate to the time of administration by a patient, caregiver, or medical professional. In one example, the kit includes a capsule comprising a suitable amount of urea powder to mix with the topical clobetasol composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% clobetasol. According to one example, the kit includes a dosage unit for formulating the compounded composition comprising a capsule containing 500 mg urea powder and 2.5 g of a 0.05% topical clobetasol composition, e.g., Clobetasol Propionate Cream, 0.05%, Clobetasol Propionate Ointment, 0.05%, Clobetasol Propionate Lotion, 0.05%, or Clobetasol Propionate Gel, 0.05%. In another example, a kit for treating a hyperkeratotic skin condition may include a capsule comprising a suitable amount of urea powder and a suitable amount of a topical corticosteroid composition to formulate a compounded topical composition comprising approximately 20% urea and approximately 0.04% clobetasol. According to one example, the kit includes a dosage unit for formulating the compounded composition comprising a capsule containing 500 mg urea powder and 2 g of a 0.1% topical clobetasol composition, e.g., Clobetasol Propionate Cream, 0.1%. The topical clobetasol composition may be packaged in specific dosage weights or may be provided in multi-dose packaging, e.g., 160 g, 150 g, 120 g, 100 g, 60 g, 30 g, 15 g tubes. In one embodiment, the kit may include urea cream and a topical clobetasol composition, e.g., Clobetasol Propionate Cream, 0.05%, Clobetasol Propionate Ointment, 0.05%, Clobetasol Propionate Lotion, 0.05%, or Clobetasol Propionate Gel, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising desoximetasone, which may include creams, ointments, gels, emulsions (o/w, w/o), foams, sprays/solutions.

In one example the topical corticosteroid composition comprising desoximetasone comprises desoximetasone cream. Desoximetasone cream is available as Desoximetasone Cream USP, 0.05%, wherein each gram contains 0.5 mg of desoximetasone in an emollient cream base of cetostearyl alcohol, edetate disodium, isopropyl myristate, lanolin alcohol, mineral oil, purified water, and white petrolatum. Desoximetasone cream is also available as Desoximetasone Cream USP, 0.25%, wherein each gram contains 2.5 mg of desoximetasone in an emollient cream base of cetostearyl alcohol, isopropyl myristate, lanolin alcohol, mineral oil, purified water, and white petrolatum. Additional commercially available strengths and formulations may be used according to the present disclosure.

In one example the topical corticosteroid composition comprising desoximetasone comprises desoximetasone gel. Desoximetasone gel is available as Desoximetasone Gel USP, 0.05%, wherein each gram contains 0.5 mg of desoximetasone in a gel base of carbomer 940, docusate sodium, edetate disodium, isopropyl myristate, purified water, SDAG-3 95% alcohol, and trolamine. Additional commercially available strengths and formulations may be used according to the present disclosure.

In one example the topical corticosteroid composition comprising desoximetasone comprises desoximetasone ointment. Desoximetasone ointment is available as Desoximetasone Ointment USP, 0.25%, wherein each gram contains 2.5 mg of desoximetasone in an ointment base of fractionated coconut oil and white petrolatum. Desoximetasone ointment is also available as Desoximetasone Ointment USP, 0.05%, wherein each gram contains 0.5 mg of desoximetasone USP in an ointment base of mineral oil and white petrolatum. Additional commercially available strengths and formulations may be used according to the present disclosure.

In various embodiments, the compounded topical composition comprises between approximately 2.5% and approximately 50% urea by weight and between approximately 0.025% and approximately 0.0488% desoximetasone by weight, such as between approximately 2.5% and approximately 25% urea by weight and between approximately 0.0350% and approximately 0.0488% desoximetasone by weight, between approximately 0.0250% and approximately 0.0375% desoximetasone by weight, between approximately 0.0325% and approximately 0.0425% desoximetasone by weight, or between approximately 0.0275% and approximately 0.0350% desoximetasone by weight; between approximately 10% and approximately 35% urea by weight and between approximately 0.0350% and approximately 0.0488% desoximetasone by weight, between approximately 0.0250% and approximately 0.0375% desoximetasone by weight, between approximately 0.0325% and approximately 0.0425% desoximetasone by weight, or between approximately 0.0275% and approximately 0.0350% desoximetasone by weight; between approximately 15% and approximately 25% urea by weight and between approximately 0.0350% and approximately 0.0488% desoximetasone by weight, between approximately 0.0250% and approximately 0.0375% desoximetasone by weight, between approximately 0.0325% and approximately 0.0425% desoximetasone by weight, or between approximately 0.0275% and approximately 0.0350% desoximetasone by weight; between approximately 25% and approximately 40% urea by weight and between approximately 0.0350% and approximately 0.0488% desoximetasone by weight, between approximately 0.0250% and approximately 0.0375% desoximetasone by weight, between approximately 0.0325% and approximately 0.0425% desoximetasone by weight, or between approximately 0.0275% and approximately 0.0350% desoximetasone by weight; or between approximately 30% and approximately 50% urea by weight and between approximately 0.0350% and approximately 0.0488% desoximetasone by weight, between approximately 0.0250% and approximately 0.0375% desoximetasone by weight, between approximately 0.0325% and approximately 0.0425% desoximetasone by weight, or between approximately 0.0275% and approximately 0.0350% desoximetasone by weight.

In various embodiments, the compounded topical composition comprises between approximately 2.5% and approximately 50% urea by weight and between approximately 0.125% and approximately 0.250% desoximetasone by weight, such as between approximately 2.5% and approximately 25% urea by weight and between approximately 0.200% and approximately 0.250% desoximetasone by weight, between approximately 0.125% and approximately 0.200% desoximetasone by weight, between approximately 0.175% and approximately 0.225% desoximetasone by weight, or between approximately 0.160% and approximately 0.215% desoximetasone by weight; between approximately 10% and approximately 35% urea by weight and between approximately 0.200% and approximately 0.250% desoximetasone by weight, between approximately 0.125% and approximately 0.200% desoximetasone by weight, between approximately 0.175% and approximately 0.225% desoximetasone by weight, or between approximately 0.160% and approximately 0.215% desoximetasone by weight; between approximately 15% and approximately 25% urea by weight and between approximately 0.200% and approximately 0.250% desoximetasone by weight, between approximately 0.125% and approximately 0.200% desoximetasone by weight, between approximately 0.175% and approximately 0.225% desoximetasone by weight, or between approximately 0.160% and approximately 0.215% desoximetasone by weight; between approximately 25% and approximately 40% urea by weight and between approximately 0.200% and approximately 0.250% desoximetasone by weight, between approximately 0.125% and approximately 0.200% desoximetasone by weight, between approximately 0.175% and approximately 0.225% desoximetasone by weight, or between approximately 0.160% and approximately 0.215% desoximetasone by weight; or between approximately 30% and approximately 50% urea by weight and between approximately 0.200% and approximately 0.250% desoximetasone by weight, between approximately 0.125% and approximately 0.200% desoximetasone by weight, between approximately 0.175% and approximately 0.225% desoximetasone by weight, or between approximately 0.160% and approximately 0.215% desoximetasone by weight.

In various embodiments, the compounded composition is provided in a kit for treating a hyperkeratotic skin condition including a capsule containing urea powder and a commercially available corticosteroid topical composition comprising desoximetasone, e.g., desoximetasone cream, ointment, or gel that may be compounded proximate to the time of administration by a patient, caregiver, or medical professional. In one example, the kit includes a capsule comprising a suitable amount of urea powder to mix with the topical desoximetasone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% desoximetasone. According to one example, the kit includes a dosage unit for formulating the compounded composition comprising a capsule containing 500 mg urea powder and 2.5 g of a 0.05% topical desoximetasone composition, e.g., Desoximetasone Cream USP, 0.05%, Desoximetasone Ointment USP, 0.05%, or Desoximetasone Gel USP, 0.05%. In another example, a kit for treating a hyperkeratotic skin condition may include a capsule comprising a suitable amount of urea powder and a suitable amount of a topical corticosteroid composition to formulate a compounded topical composition comprising approximately 20% urea and approximately 0.200% desoximetasone may include a capsule containing 600 mg urea powder and 2.4 g of a 0.25% topical desoximetasone composition, e.g., Desoximetasone Cream USP, 0.25%, or Desoximetasone Ointment USP, 0.25%. The topical desoximetasone composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical desoximetasone composition, e.g., Desoximetasone Cream USP, 0.05%, Desoximetasone Ointment USP, 0.05%, Desoximetasone Gel USP, 0.05%, Desoximetasone Cream USP, 0.25%, or Desoximetasone Ointment USP, 0.25%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising diflorasone composition, which may include creams, ointments, gels, emulsions (o/w, w/o), foams, sprays/solutions.

In one example the topical corticosteroid composition comprising diflorasone topical corticosteroid comprises diflorasone diacetate cream. Diflorasone diacetate cream is available as Diflorasone Diacetate Cream USP, 0.05%, wherein each gram contains 0.5 mg diflorasone diacetate in a cream base of cetyl alcohol, glyceryl stearate SE (nonionic), isopropyl myristate, mineral oil (and) lanolin alcohol, monobasic sodium phosphate, monoglyceride citrate, polyoxyl 40 stearate, polysorbate 60, propylene glycol, purified water, sorbitan monostearate, vegetable oil, butylated hydroxytoluene and citric acid. Additional commercially available strengths and formulations may be used according to the present disclosure.

In one example the topical corticosteroid composition comprising diflorasone topical corticosteroid comprises diflorasone diacetate cream comprising emollient. Diflorasone diacetate cream comprising emollient is also available as Diflorasone Diacetate Cream USP, 0.05%, (Emollient) wherein each gram contains 0.5 mg Diflorasone diacetate in a hydrophilic vanishing cream base of propylene glycol, stearyl alcohol, cetyl alcohol, sorbitan monostearate, polysorbate 60, mineral oil and purified water. Additional commercially available strengths and formulations may be used according to the present disclosure.

In one example the topical corticosteroid composition comprising diflorasone topical corticosteroid comprises diflorasone diacetate ointment. Diflorasone diacetate ointment is available as Diflorasone Diacetate Ointment USP, 0.05%, wherein each gram contains 0.5 mg diflorasone diacetate in an ointment base of propylene glycol, glyceryl monostearate and white petrolatum. Additional commercially available strengths and formulations may be used according to the present disclosure.

In various embodiments, the compounded topical composition comprises between approximately 2.5% and approximately 50% urea by weight and between approximately 0.025% and approximately 0.0488% diflorasone by weight, such as between approximately 2.5% and approximately 25% urea by weight and between approximately 0.0350% and approximately 0.0488% diflorasone by weight, between approximately 0.0250% and approximately 0.0375% diflorasone by weight, between approximately 0.0325% and approximately 0.0425% diflorasone by weight, or between approximately 0.0275% and approximately 0.0350% diflorasone by weight; between approximately 10% and approximately 35% urea by weight and between approximately 0.0350% and approximately 0.0488% diflorasone by weight, between approximately 0.0250% and approximately 0.0375% diflorasone by weight, between approximately 0.0325% and approximately 0.0425% diflorasone by weight, or between approximately 0.0275% and approximately 0.0350% diflorasone by weight; between approximately 15% and approximately 25% urea by weight and between approximately 0.0350% and approximately 0.0488% diflorasone by weight, between approximately 0.0250% and approximately 0.0375% diflorasone by weight, between approximately 0.0325% and approximately 0.0425% diflorasone by weight, or between approximately 0.0275% and approximately 0.0350% diflorasone by weight; between approximately 25% and approximately 40% urea by weight and between approximately 0.0350% and approximately 0.0488% diflorasone by weight, between approximately 0.0250% and approximately 0.0375% diflorasone by weight, between approximately 0.0325% and approximately 0.0425% diflorasone by weight, or between approximately 0.0275% and approximately 0.0350% diflorasone by weight; or between approximately 30% and approximately 50% urea by weight and between approximately 0.0350% and approximately 0.0488% diflorasone by weight, between approximately 0.0250% and approximately 0.0375% diflorasone by weight, between approximately 0.0325% and approximately 0.0425% diflorasone by weight, or between approximately 0.0275% and approximately 0.0350% diflorasone by weight.

In various embodiments, the compounded composition is provided in a kit for treating a hyperkeratotic skin condition including a capsule containing urea powder and a commercially available corticosteroid topical composition comprising diflorasone, e.g., diflorasone cream, ointment, or cream, that may be compounded proximate to the time of administration by a patient, caregiver, or medical professional. In one example, the kit includes a capsule comprising a suitable amount of urea powder to mix with the topical diflorasone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% diflorasone. According to one example, the kit includes a dosage unit for formulating the compounded composition comprising a capsule containing 500 mg urea powder and 2.5 g of a 0.05% topical diflorasone composition, e.g., Diflorasone Diacetate Cream USP, 0.05% or Diflorasone Diacetate Ointment USP, 0.05%. The topical diflorasone composition may be packaged in specific dosage weights or may be provided in multi-dose packaging, e.g., 160 g, 150 g, 120 g, 100 g, 60 g, 30 g, 15 g tubes. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising flurandrenolide, which may include creams, ointments, gels, emulsions (o/w, w/o), foams, sprays/solutions.

In one example the topical corticosteroid composition comprising flurandrenolide topical corticosteroid comprises flurandrenolide cream. Flurandrenolide cream is available as Flurandrenolide Cream USP, 0.05%, wherein each gram contains 0.5 mg (1.145 µmol; 0.05%) flurandrenolide in an emulsified base composed of cetyl alcohol, citric acid, mineral oil, polyoxyl 40 stearate, propylene glycol, sodium citrate, stearic acid, and purified water. Flurandrenolide cream is also available as Flurandrenolide Cream USP, 0.025%, wherein each gram contains 0.25 mg (0.57 µmol; 0.025%) flurandrenolide in an emulsified base composed of cetyl alcohol, citric acid, mineral oil, polyoxyl 40 stearate, propylene glycol, sodium citrate, stearic acid, and purified water. Additional commercially available strengths and formulations may be used according to the present disclosure.

In one example the topical corticosteroid composition comprising flurandrenolide topical corticosteroid comprises flurandrenolide lotion. Flurandrenolide lotion is available as Flurandrenolide Lotion, USP 0.05%, wherein each gram contains 0.5 mg (1.145 µmol) (0.05%) flurandrenolide in an oil-in-water emulsion base composed of glycerin, cetyl alcohol, stearic acid, glyceryl monostearate, mineral oil, polyoxyl 40 stearate, menthol, benzyl alcohol, and purified water. Additional commercially available strengths and formulations may be used according to the present disclosure.

In one example the topical corticosteroid composition comprising flurandrenolide topical corticosteroid comprises flurandrenolide ointment. Flurandrenolide ointment is available as flurandrenolide Ointment USP, 0.05%, wherein each gram contains 0.5 mg (1.145 µmol; 0.05%) flurandrenolide in a base composed of white wax, cetyl alcohol, sorbitan sesquioleate, and white petrolatum. Flurandrenolide ointment is also available as Flurandrenolide Ointment USP, 0.025% wherein each gram contains 0.25 mg (0.57 µmol; 0.025%) flurandrenolide in a base composed of white wax, cetyl alcohol, sorbitan sesquioleate, and white petrolatum. Additional commercially available strengths and formulations may be used according to the present disclosure.

In various embodiments, the compounded topical composition comprises between approximately 2.5% and approximately 50% urea by weight and between approximately 0.025% and approximately 0.0488% flurandrenolide by weight, such as between approximately 2.5% and approximately 25% urea by weight and between approximately 0.0350% and approximately 0.0488% flurandrenolide by weight, between approximately 0.0250% and approximately 0.0375% flurandrenolide by weight, between approximately 0.0325% and approximately 0.0425% flurandrenolide by weight, or between approximately 0.0275% and approximately 0.0350% flurandrenolide by weight; between approximately 10% and approximately 35% urea by weight and between approximately 0.0350% and approximately 0.0488% flurandrenolide by weight, between approximately 0.0250% and approximately 0.0375% flurandrenolide by weight, between approximately 0.0325% and approximately 0.0425% flurandrenolide by weight, or between approximately 0.0275% and approximately 0.0350% flurandrenolide by weight; between approximately 15% and approximately 25% urea by weight and between approximately 0.0350% and approximately 0.0488% flurandrenolide by weight, between approximately 0.0250% and approximately 0.0375% flurandrenolide by weight, between approximately 0.0325% and approximately 0.0425% flurandrenolide by weight, or between approximately 0.0275% and approximately 0.0350% flurandrenolide by weight; between approximately 25% and approximately 40% urea by weight and between approximately 0.0350% and approximately 0.0488% flurandrenolide by weight, between approximately 0.0250% and approximately 0.0375% flurandrenolide by weight, between approximately 0.0325% and approximately 0.0425% flurandrenolide by weight, or between approximately 0.0275% and approximately 0.0350% flurandrenolide by weight; or between approximately 30% and approximately 50% urea by weight and between approximately 0.0350% and approximately 0.0488% flurandrenolide by weight, between approximately 0.0250% and approximately 0.0375% flurandrenolide by weight, between approximately 0.0325% and approximately 0.0425% flurandrenolide by weight, or between approximately 0.0275% and approximately 0.0350% flurandrenolide by weight.

In various embodiments, the compounded topical composition comprises between approximately 2.5% and approximately 50% urea by weight and between approximately 0.0125% and approximately 0.0250% flurandrenolide by weight, such as between approximately 2.5% and approximately 25% urea by weight and between approximately 0.0200% and approximately 0.0250% flurandrenolide by weight, between approximately 0.0125% and approximately 0.0200% flurandrenolide by weight, between approximately 0.0175% and approximately 0.0225% flurandrenolide by weight, or between approximately 0.0160% and approximately 0.0215% flurandrenolide by weight; between approximately 10% and approximately 35% urea by weight and between approximately 0.0200% and approximately 0.0250% flurandrenolide by weight, between approximately 0.0125% and approximately 0.0200% flurandrenolide by weight, between approximately 0.0175% and approximately 0.0225% flurandrenolide by weight, or between approximately 0.0160% and approximately 0.0215% flurandrenolide by weight; between approximately 15% and approximately 25% urea by weight and between approximately 0.0200% and approximately 0.0250% flurandrenolide by weight, between approximately 0.0125% and approximately 0.0200% flurandrenolide by weight, between approximately 0.0175% and approximately 0.0225% flurandrenolide by weight, or between approximately 0.0160% and approximately 0.0215% flurandrenolide by weight; between approximately 25% and approximately 40% urea by weight and between approximately 0.0200% and approximately 0.0250% flurandrenolide by weight, between approximately 0.0125% and approximately 0.0200% flurandrenolide by weight, between approximately 0.0175% and approximately 0.0225% flurandrenolide by weight, or between approximately 0.0160% and approximately 0.0215% flurandrenolide by weight; or between approximately 30% and approximately 50% urea by weight and between approximately 0.0200% and approximately 0.0250% flurandrenolide by weight, between approximately 0.0125% and approximately 0.0200% flurandrenolide by weight, between approximately 0.0175% and approximately 0.0225% flurandrenolide by weight, or between approximately 0.0160% and approximately 0.0215% flurandrenolide by weight.

In various embodiments, the compounded composition is provided in a kit for treating a hyperkeratotic skin condition including a capsule containing urea powder and a commercially available corticosteroid topical composition comprising flurandrenolide, e.g., flurandrenolide cream, ointment, or lotion, that may be compounded proximate to the time of administration by a patient, caregiver, or medical professional. In one example, the kit includes a capsule comprising a suitable amount of urea powder to mix with the topical flurandrenolide composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% flurandrenolide. According to one example, the kit includes a dosage unit for formulating the compounded composition comprising a capsule containing 500 mg urea powder and 2.5 g of a 0.05% topical flurandrenolide composition, e.g., Flurandrenolide Cream USP, 0.05%, Flurandrenolide Ointment USP, 0.05%, or Flurandrenolide Lotion USP, 0.05%. In another example, a kit for treating a hyperkeratotic skin condition may include a capsule comprising a suitable amount of urea powder and a suitable amount of a topical corticosteroid composition to formulate a compounded topical composition comprising approximately 20% urea and approximately 0.200% flurandrenolide may include a capsule containing 600 mg urea powder and 2.4 g of a 0.025% topical flurandrenolide composition, e.g., Flurandrenolide Cream USP, 0.025%, or Flurandrenolide Ointment USP, 0.025%. The topical flurandrenolide composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical flurandrenolide composition, e.g., Flurandrenolide Cream USP, 0.05%, Flurandrenolide Ointment USP, 0.05%, Flurandrenolide Lotion USP, 0.05%, Flurandrenolide Cream USP, 0.025%, or Flurandrenolide Ointment USP, 0.025%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising fluticasone, which may include creams, ointments, gels, emulsions (o/w, w/o), foams, sprays/solutions.

In one example the topical corticosteroid composition comprising fluticasone topical corticosteroid comprises fluticasone cream. Fluticasone cream is available as Fluticasone Propionate Cream, USP 0.05%, wherein each gram contains fluticasone propionate 0.5 mg in a base of propylene glycol, mineral oil, cetostearyl alcohol, Ceteth-20, isopropyl myristate, dibasic sodium phosphate, citric acid, purified water, and methylparaben as preservative. Additional commercially available strengths and formulations may be used according to the present disclosure.

In various embodiments, the compounded topical composition comprises between approximately 2.5% and approximately 50% urea by weight and between approximately 0.025% and approximately 0.0488% fluticasone by weight, such as between approximately 2.5% and approximately 25% urea by weight and between approximately 0.0350% and approximately 0.0488% fluticasone by weight, between approximately 0.0250% and approximately 0.0375% fluticasone by weight, between approximately 0.0325% and approximately 0.0425% fluticasone by weight, or between approximately 0.0275% and approximately 0.0350% fluticasone by weight; between approximately 10% and approximately 35% urea by weight and between approximately 0.0350% and approximately 0.0488% fluticasone by weight, between approximately 0.0250% and approximately 0.0375% fluticasone by weight, between approximately 0.0325% and approximately 0.0425% fluticasone by weight, or between approximately 0.0275% and approximately 0.0350% fluticasone by weight; between approximately 15% and approximately 25% urea by weight and between approximately 0.0350% and approximately 0.0488% fluticasone by weight, between approximately 0.0250% and approximately 0.0375% fluticasone by weight, between approximately 0.0325% and approximately 0.0425% fluticasone by weight, or between approximately 0.0275% and approximately 0.0350% fluticasone by weight; between approximately 25% and approximately 40% urea by weight and between approximately 0.0350% and approximately 0.0488% fluticasone by weight, between approximately 0.0250% and approximately 0.0375% fluticasone by weight, between approximately 0.0325% and approximately 0.0425% fluticasone by weight, or between approximately 0.0275% and approximately 0.0350% fluticasone by weight; or between approximately 30% and approximately 50% urea by weight and between approximately 0.0350% and approximately 0.0488% fluticasone by weight, between approximately 0.0250% and approximately 0.0375% fluticasone by weight, between approximately 0.0325% and approximately 0.0425% fluticasone by weight, or between approximately 0.0275% and approximately 0.0350% fluticasone by weight.

In various embodiments, the compounded composition is provided in a kit for treating a hyperkeratotic skin condition including a capsule containing urea powder and a commercially available corticosteroid topical composition comprising fluticasone, e.g., fluticasone cream or ointment, that may be compounded proximate to the time of administration by a patient, caregiver, or medical professional. In one example, the kit includes a capsule comprising a suitable amount of urea powder to mix with the topical fluticasone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% fluticasone. According to one example, the kit includes a dosage unit for formulating the compounded composition comprising a capsule containing 500 mg urea powder and 2.5 g of a 0.05% topical fluticasone composition, e.g., Fluticasone Propionate Cream USP, 0.05%. The topical fluticasone composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical fluticasone composition, e.g., Fluticasone Propionate Cream USP, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising fluocinonide, which may include creams, ointments, gels, emulsions (o/w, w/o), foams, sprays/solutions.

In one example the topical corticosteroid composition comprising fluticasone topical corticosteroid comprises fluocinonide cream. Fluocinonide cream is available as Fluocinonide Cream USP, 0.1%, wherein each gram contains 1 mg fluocinonide in a cream base of propylene glycol USP, diethylene glycol monoethyl ether NF, glyceryl stearate (and) PEG-100 stearate, purified water USP, glyceryl monostearate NF, white petrolatum USP, carbomer 980 NF, diisopropanolamine, and citric acid USP. Fluocinonide cream is also available as fluocinonide cream USP, 0.05% contains fluocinonide 0.5 mg/g in a cream base of citric acid, 1,2,6-hexanetriol, polyethylene glycol-8000, propylene glycol and stearyl alcohol. This white cream vehicle is greaseless, non-staining, anhydrous and completely water miscible. The base provides emollient and hydrophilic properties. Fluocinonide cream is also available as Fluocinonide Cream (Emulsified Base), 0.05%, containing fluocinonide 0.5 mg/g in a water-washable aqueous emollient base of cetyl alcohol, citric acid, mineral oil, polysorbate 60, propylene glycol, sorbitan monostearate, stearyl alcohol and water (purified). Additional commercially available strengths and formulations may be used according to the present disclosure. Additional commercially available strengths and formulations may be used according to the present disclosure.

In one example the topical corticosteroid composition comprising fluticasone topical corticosteroid comprises fluocinonide gel. Fluocinonide gel is available as Fluocinonide Gel USP, 0.05%, containing fluocinonide 0.5 mg/g in a gel base of carbomer 940, edetate disodium, propyl gallate, propylene glycol, sodium hydroxide (to adjust pH) and purified water. This clear, colorless, thixotropic vehicle is greaseless, non-staining and completely water miscible. Additional commercially available strengths and formulations may be used according to the present disclosure. Additional commercially available strengths and formulations may be used according to the present disclosure.

In one example the topical corticosteroid composition comprising fluticasone topical corticosteroid comprises fluocinonide ointment. Fluocinonide ointment is available as Fluocinonide Ointment USP, 0.05%, containing fluocinonide 0.5 mg/g in an ointment base of glyceryl monostearate, propylene carbonate, propylene glycol, white petrolatum and white wax. It provides the occlusive and emollient effects desirable in an ointment. Additional commercially available strengths and formulations may be used according to the present disclosure. Additional commercially available strengths and formulations may be used according to the present disclosure.

In various embodiments, the compounded topical composition comprises between approximately 2.5% and approximately 50% urea by weight and between approximately 0.05% and approximately 0.098% fluocinonide by weight, such as between approximately 2.5% and approximately 25% urea by weight and between approximately 0.075% and approximately 0.098% fluocinonide by weight, between approximately 0.05% and approximately 0.075% fluocinonide by weight, between approximately 0.065% and approximately 0.085% fluocinonide by weight, or between approximately 0.06% and approximately 0.07% fluocinonide by weight; between approximately 10% and approximately 35% urea by weight and between approximately 0.075% and approximately 0.098% fluocinonide by weight, between approximately 0.05% and approximately 0.075% fluocinonide by weight, between approximately 0.065% and approximately 0.085% fluocinonide by weight, or between approximately 0.06% and approximately 0.07% fluocinonide by weight; between approximately 15% and approximately 25% urea by weight and between approximately 0.075% and approximately 0.098% fluocinonide by weight, between approximately 0.05% and approximately 0.075% fluocinonide by weight, between approximately 0.065% and approximately 0.085% fluocinonide by weight, or between approximately 0.06% and approximately 0.07% fluocinonide by weight; between approximately 25% and approximately 40% urea by weight and between approximately 0.075% and approximately 0.098% fluocinonide by weight, between approximately 0.05% and approximately 0.075% fluocinonide by weight, between approximately 0.065% and approximately 0.085% fluocinonide by weight, or between approximately 0.06% and approximately 0.07% fluocinonide by weight; or between approximately 30% and approximately 50% urea by weight and between approximately 0.075% and approximately 0.098% fluocinonide by weight, between approximately 0.05% and approximately 0.075% fluocinonide by weight, between approximately 0.065% and approximately 0.085% fluocinonide by weight, or between approximately 0.06% and approximately 0.07% fluocinonide by weight.

In various embodiments, the compounded topical composition comprises between approximately 2.5% and approximately 50% urea by weight and between approximately 0.025% and approximately 0.0488% fluocinonide by weight, such as between approximately 2.5% and approximately 25% urea by weight and between approximately 0.0350% and approximately 0.0488% fluocinonide by weight, between approximately 0.0250% and approximately 0.0375% fluocinonide by weight, between approximately 0.0325% and approximately 0.0425% fluocinonide by weight, or between approximately 0.0275% and approximately 0.0350% fluocinonide by weight; between approximately 10% and approximately 35% urea by weight and between approximately 0.0350% and approximately 0.0488% fluocinonide by weight, between approximately 0.0250% and approximately 0.0375% fluocinonide by weight, between approximately 0.0325% and approximately 0.0425% fluocinonide by weight, or between approximately 0.0275% and approximately 0.0350% fluocinonide by weight; between approximately 15% and approximately 25% urea by weight and between approximately 0.0350% and approximately 0.0488% fluocinonide by weight, between approximately 0.0250% and approximately 0.0375% fluocinonide by weight, between approximately 0.0325% and approximately 0.0425% fluocinonide by weight, or between approximately 0.0275% and approximately 0.0350% fluocinonide by weight; between approximately 25% and approximately 40% urea by weight and between approximately 0.0350% and approximately 0.0488% fluocinonide by weight, between approximately 0.0250% and approximately 0.0375% fluocinonide by weight, between approximately 0.0325% and approximately 0.0425% fluocinonide by weight, or between approximately 0.0275% and approximately 0.0350% fluocinonide by weight; or between approximately 30% and approximately 50% urea by weight and between approximately 0.0350% and approximately 0.0488% fluocinonide by weight, between approximately 0.0250% and approximately 0.0375% fluocinonide by weight, between approximately 0.0325% and approximately 0.0425% fluocinonide by weight, or between approximately 0.0275% and approximately 0.0350% fluocinonide by weight.

In various embodiments, the compounded composition is provided in a kit for treating a hyperkeratotic skin condition including a capsule containing urea powder and a commercially available corticosteroid topical composition comprising fluocinonide, e.g., cream, ointment, or gel, that may be compounded proximate to the time of administration by a patient, caregiver, or medical professional. In one example, the kit includes a capsule comprising a suitable amount of urea powder to mix with the topical fluocinonide composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% fluocinonide. According to one example, the kit includes a dosage unit for formulating the compounded composition comprising a capsule containing 500 mg urea powder and 2.5 g of a 0.05% topical fluocinonide composition, e.g., Fluocinonide Cream USP, 0.05%, Fluocinonide Ointment USP, 0.05%, or Fluocinonide Gel USP, 0.05%. In another example, a kit for treating a hyperkeratotic skin condition may include a capsule comprising a suitable amount of urea powder and a suitable amount of a topical corticosteroid composition to formulate a compounded topical composition comprising approximately 20% urea and 0.08% fluocinonide. According to one example, the kit includes a dosage unit for formulating the compounded composition comprising a capsule containing 500 mg urea powder and 2 g of a 0.1% topical fluocinonide composition, e.g., Fluocinonide Cream USP, 0.1%. The topical fluocinonide composition may be packaged in specific dosage weights or may be provided in multi-dose packaging, e.g., 160 g, 150 g, 120 g, 100 g, 60 g, 30 g, 15 g tubes.

In one embodiment, a kit may include urea cream and a topical fluocinonide composition, e.g., Fluocinonide Cream USP, 0.05%, Fluocinonide Ointment USP, 0.05%, or Fluocinonide Gel USP, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising halcinonide, which may include creams, ointments, gels, emulsions (o/w, w/o), foams, sprays/solutions.

In one example the topical corticosteroid composition comprising halcinonide topical corticosteroid comprises halcinonide cream. Halcinonide cream is available as Halcinonide Cream, USP 0.1%, wherein each gram contains 1 mg halcinonide, USP in a cream base of cetyl alcohol, dimethicone 350, glyceryl monostearate, isopropyl palmitate, polysorbate 60, propylene glycol, purified water, and titanium dioxide. Additional commercially available strengths and formulations may be used according to the present disclosure.

In one example the topical corticosteroid composition comprising halcinonide topical corticosteroid comprises halcinonide ointment. Halcinonide Ointment is available as Halcinonide Ointment, USP 0.1%, wherein each gram contains 1 mg halcinonide in Plasticized Hydrocarbon Gel, a mineral oil and polyethylene gel base, polyethylene glycol 300, polyethylene glycol 400, polyethylene glycol 1450, and polyethylene glycol 6000 distearate with butylated hydroxytoluene as an antioxidant. Additional commercially available strengths and formulations may be used according to the present disclosure.

In various embodiments, the compounded topical composition comprises between approximately 2.5% and approximately 50% urea by weight and between approximately 0.05% and approximately 0.098% halcinonide by weight, such as between approximately 2.5% and approximately 25% urea by weight and between approximately 0.075% and approximately 0.098% halcinonide by weight, between approximately 0.05% and approximately 0.075% halcinonide by weight, between approximately 0.065% and approximately 0.085% halcinonide by weight, or between approximately 0.06% and approximately 0.07% halcinonide by weight; between approximately 10% and approximately 35% urea by weight and between approximately 0.075% and approximately 0.098% halcinonide by weight, between approximately 0.05% and approximately 0.075% halcinonide by weight, between approximately 0.065% and approximately 0.085% halcinonide by weight, or between approximately 0.06% and approximately 0.07% halcinonide by weight; between approximately 15% and approximately 25% urea by weight and between approximately 0.075% and approximately 0.098% halcinonide by weight, between approximately 0.05% and approximately 0.075% halcinonide by weight, between approximately 0.065% and approximately 0.085% halcinonide by weight, or between approximately 0.06% and approximately 0.07% halcinonide by weight; between approximately 25% and approximately 40% urea by weight and between approximately 0.075% and approximately 0.098% halcinonide by weight, between approximately 0.05% and approximately 0.075% halcinonide by weight, between approximately 0.065% and approximately 0.085% halcinonide by weight, or between approximately 0.06% and approximately 0.07% halcinonide by weight; or between approximately 30% and approximately 50% urea by weight and between approximately 0.075% and approximately 0.098% halcinonide by weight, between approximately 0.05% and approximately 0.075% halcinonide by weight, between approximately 0.065% and approximately 0.085% halcinonide by weight, or between approximately 0.06% and approximately 0.07% halcinonide by weight.

In various embodiments, the compounded composition is provided in a kit for treating a hyperkeratotic skin condition including a capsule containing urea powder and a commercially available corticosteroid topical composition comprising halcinonide, e.g., cream or ointment, that may be compounded proximate to the time of administration by a patient, caregiver, or medical professional. In one example, the kit includes a capsule comprising a suitable amount of urea powder to mix with the topical halcinonide composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 20% urea and 0.08% halcinonide. According to one example, the kit includes a dosage unit for formulating the compounded composition comprising a capsule containing 500 mg urea powder and 2 g of a 0.1% topical halcinonide composition, e.g., Halcinonide Cream USP, 0.1%, Halcinonide Ointment USP, 0.1%. The topical halcinonide composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical halcinonide composition, e.g., Halcinonide Cream USP, 0.1% or Halcinonide Ointment USP, 0.1%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising halobetasol, which may include creams, ointments, gels, emulsions (o/w, w/o), foams, sprays/solutions.

In one example the topical corticosteroid composition comprising halobetasol topical corticosteroid comprises halobetasol cream. Halobetasol propionate cream is available as Halobetasol Propionate Cream, 0.05%, containing 0.5 mg/g of halobetasol propionate in a cream base of cetyl alcohol, glycerin, isopropyl isostearate, isopropyl palmitate, steareth-21, diazolidinyl urea, methylchloroisothiazolinone, (and) methylisothiazolinone and water. Additional commercially available strengths and formulations may be used according to the present disclosure.

In one example the topical corticosteroid composition comprising halobetasol topical corticosteroid comprises halobetasol ointment. Halobetasol propionate ointment is available as Halobetasol Propionate Ointment, 0.05%, containing 0.5 mg/g of halobetasol propionate in a base of aluminum stearate, beeswax, pentaerythritol cocoate, petrolatum, propylene glycol, sorbitan sesquioleate, and stearyl citrate. Additional commercially available strengths and formulations may be used according to the present disclosure.

In one example the topical corticosteroid composition comprising halobetasol topical corticosteroid comprises halobetasol lotion. Halobetasol propionate lotion is available as Halobetasol Propionate Lotion, 0.05%, containing 0.5 mg of halobetasol propionate in a white to off-white lotion base of diisopropyl adipate, octyldodecanol, ceteth-20, poloxamer 407, cetyl alcohol, stearyl alcohol, propylparaben, butylparaben, propylene glycol, glycerin, carbomer homopolymer, sodium hydroxide, and water. Additional commercially available strengths and formulations may be used according to the present disclosure.

In various embodiments, the compounded topical composition comprises between approximately 2.5% and approximately 50% urea by weight and between approximately 0.025% and approximately 0.0488% halobetasol by weight, such as between approximately 2.5% and approximately 25% urea by weight and between approximately 0.0350% and approximately 0.0488% halobetasol by weight, between approximately 0.0250% and approximately 0.0375% halobetasol by weight, between approximately 0.0325% and approximately 0.0425% halobetasol by weight, or between approximately 0.0275% and approximately 0.0350% halobetasol by weight; between approximately 10% and approximately 35% urea by weight and between approximately 0.0350% and approximately 0.0488% halobetasol by weight, between approximately 0.0250% and approximately 0.0375% halobetasol by weight, between approximately 0.0325% and approximately 0.0425% halobetasol by weight, or between approximately 0.0275% and approximately 0.0350% halobetasol by weight; between approximately 15% and approximately 25% urea by weight and between approximately 0.0350% and approximately 0.0488% halobetasol by weight, between approximately 0.0250% and approximately 0.0375% halobetasol by weight, between approximately 0.0325% and approximately 0.0425% halobetasol by weight, or between approximately 0.0275% and approximately 0.0350% halobetasol by weight; between approximately 25% and approximately 40% urea by weight and between approximately 0.0350% and approximately 0.0488% halobetasol by weight, between approximately 0.0250% and approximately 0.0375% halobetasol by weight, between approximately 0.0325% and approximately 0.0425% halobetasol by weight, or between approximately 0.0275% and approximately 0.0350% halobetasol by weight; or between approximately 30% and approximately 50% urea by weight and between approximately 0.0350% and approximately 0.0488% halobetasol by weight, between approximately 0.0250% and approximately 0.0375% halobetasol by weight, between approximately 0.0325% and approximately 0.0425% halobetasol by weight, or between approximately 0.0275% and approximately 0.0350% halobetasol by weight.

In various embodiments, the compounded composition is provided in a kit for treating a hyperkeratotic skin condition including a capsule containing urea powder and a commercially available corticosteroid topical composition comprising halobetasol, e.g., halobetasol cream, ointment, or lotion, that may be compounded proximate to the time of administration by a patient, caregiver, or medical professional. In one example, the kit includes a capsule comprising a suitable amount of urea powder to mix with the topical halobetasol composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% halobetasol. According to one example, the kit includes a dosage unit for formulating the compounded composition comprising a capsule containing 500 mg urea powder and 2.5 g of a 0.05% topical halobetasol composition, e.g., Halobetasol Propionate Cream, 0.05%, Halobetasol Propionate Ointment, 0.05%, Halobetasol Propionate Lotion, 0.05%. The topical halobetasol composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical halobetasol composition, e.g., Halobetasol Propionate Cream, 0.05%, Halobetasol Propionate Ointment, 0.05%, Halobetasol Propionate Lotion, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising mometasone, which may include creams, ointments, gels, emulsions (o/w, w/o), foams, sprays/solutions.

In one example the topical corticosteroid composition comprising mometasone topical corticosteroid comprises mometasone cream. Mometasone furoate cream is available as Mometasone Furoate Cream USP, 0.1%, wherein each gram contains 1 mg mometasone furoate in a white to off-white uniform cream base of aluminum starch octenylsuccinate, ceteareth-20, phosphoric acid, propylene glycol, propylene glycol stearate, purified water, stearyl alcohol, titanium dioxide, white petrolatum and white wax. Additional commercially available strengths and formulations may be used according to the present disclosure.

In one example the topical corticosteroid composition comprising mometasone topical corticosteroid comprises mometasone ointment. Mometasone furoate ointment is available as Mometasone Furoate Ointment USP, 0.1%, wherein each gram contains 1 mg mometasone furoate USP in an ointment base of hexylene glycol, phosphoric acid, propylene glycol stearate (55% monoester), white wax, white petrolatum, and purified water. Additional commercially available strengths and formulations may be used according to the present disclosure.

In various embodiments, the compounded topical composition comprises between approximately 2.5% and approximately 50% urea by weight and between approximately 0.05% and approximately 0.098% mometasone by weight, such as between approximately 2.5% and approximately 25% urea by weight and between approximately 0.075% and approximately 0.098% mometasone by weight, between approximately 0.05% and approximately 0.075% mometasone by weight, between approximately 0.065% and approximately 0.085% mometasone by weight, or between approximately 0.06% and approximately 0.07% mometasone by weight; between approximately 10% and approximately 35% urea by weight and between approximately 0.075% and approximately 0.098% mometasone by weight, between approximately 0.05% and approximately 0.075% mometasone by weight, between approximately 0.065% and approximately 0.085% mometasone by weight, or between approximately 0.06% and approximately 0.07% mometasone by weight; between approximately 15% and approximately 25% urea by weight and between approximately 0.075% and approximately 0.098% mometasone by weight, between approximately 0.05% and approximately 0.075% mometasone by weight, between approximately 0.065% and approximately 0.085% mometasone by weight, or between approximately 0.06% and approximately 0.07% mometasone by weight; between approximately 25% and approximately 40% urea by weight and between approximately 0.075% and approximately 0.098% mometasone by weight, between approximately 0.05% and approximately 0.075% mometasone by weight, between approximately 0.065% and approximately 0.085% mometasone by weight, or between approximately 0.06% and approximately 0.07% mometasone by weight; or between approximately 30% and approximately 50% urea by weight and between approximately 0.075% and approximately 0.098% mometasone by weight, between approximately 0.05% and approximately 0.075% mometasone by weight, between approximately 0.065% and approximately 0.085% mometasone by weight, or between approximately 0.06% and approximately 0.07% mometasone by weight.

In various embodiments, the compounded composition is provided in a kit for treating a hyperkeratotic skin condition including a capsule containing urea powder and a commercially available corticosteroid topical composition comprising mometasone, e.g., cream or ointment, that may be compounded proximate to the time of administration by a patient, caregiver, or medical professional. In one example, the kit includes a capsule comprising a suitable amount of urea powder to mix with the topical mometasone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 20% urea and 0.08% mometasone. According to one example, the kit includes a dosage unit for formulating the compounded composition comprising a capsule containing 500 mg urea powder and 2 g of a 0.1% topical mometasone composition, e.g., Mometasone Furoate Cream USP, 0.1%, Mometasone Furoate Ointment USP, 0.1%. The topical mometasone composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical mometasone composition, e.g., Mometasone Furoate Cream USP, 0.1% or Mometasone Furoate Ointment USP, 0.1%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In an embodiment, the compounded topical composition comprises urea powder, solution, or topical urea composition compounded with a topical corticosteroid composition comprising triamcinolone, which may include creams, ointments, gels, emulsions (o/w, w/o), foams, sprays/solutions.

In one example the topical corticosteroid composition comprising triamcinolone topical corticosteroid comprises triamcinolone cream. Triamcinolone acetonide cream is available as Triamcinolone Acetonide Cream USP, 0.1%, wherein each gram contains 1 mg triamcinolone acetonide USP in a cream base of purified water, emulsifying wax, mineral oil, propylene glycol, sorbitol solution, cetyl palmitate, sorbic acid, and potassium sorbate. Additional commercially available strengths and formulations may be used according to the present disclosure.

In one example the topical corticosteroid composition comprising triamcinolone topical corticosteroid comprises triamcinolone ointment. Triamcinolone acetonide ointment is available as Triamcinolone Acetonide Ointment USP, 0.05%, wherein each gram contains 0.5 mg of Triamcinolone Acetonide USP in a water-in-oil emulsion composed of Light Mineral Oil NF, Purified Water USP, White Petrolatum USP, Heavy Mineral Oil USP, Mineral Wax, and Lanolin Alcohols NF. The white ointment is for topical use only. Additional commercially available strengths and formulations may be used according to the present disclosure.

In various embodiments, the compounded topical composition comprises between approximately 2.5% and approximately 50% urea by weight and between approximately 0.05% and approximately 0.098% triamcinolone by weight, such as between approximately 2.5% and approximately 25% urea by weight and between approximately 0.075% and approximately 0.098% triamcinolone by weight, between approximately 0.05% and approximately 0.075% triamcinolone by weight, between approximately 0.065% and approximately 0.085% triamcinolone by weight, or between approximately 0.06% and approximately 0.07% triamcinolone by weight; between approximately 10% and approximately 35% urea by weight and between approximately 0.075% and approximately 0.098% triamcinolone by weight, between approximately 0.05% and approximately 0.075% triamcinolone by weight, between approximately 0.065% and approximately 0.085% triamcinolone by weight, or between approximately 0.06% and approximately 0.07% triamcinolone by weight; between approximately 15% and approximately 25% urea by weight and between approximately 0.075% and approximately 0.098% triamcinolone by weight, between approximately 0.05% and approximately 0.075% triamcinolone by weight, between approximately 0.065% and approximately 0.085% triamcinolone by weight, or between approximately 0.06% and approximately 0.07% triamcinolone by weight; between approximately 25% and approximately 40% urea by weight and between approximately 0.075% and approximately 0.098% triamcinolone by weight, between approximately 0.05% and approximately 0.075% triamcinolone by weight, between approximately 0.065% and approximately 0.085% triamcinolone by weight, or between approximately 0.06% and approximately 0.07% triamcinolone by weight; or between approximately 30% and approximately 50% urea by weight and between approximately 0.075% and approximately 0.098% triamcinolone by weight, between approximately 0.05% and approximately 0.075% triamcinolone by weight, between approximately 0.065% and approximately 0.085% triamcinolone by weight, or between approximately 0.06% and approximately 0.07% triamcinolone by weight.

In various embodiments, the compounded topical composition comprises between approximately 2.5% and approximately 50% urea by weight and between approximately 0.025% and approximately 0.0488% triamcinolone by weight, such as between approximately 2.5% and approximately 25% urea by weight and between approximately 0.0350% and approximately 0.0488% triamcinolone by weight, between approximately 0.0250% and approximately 0.0375% triamcinolone by weight, between approximately 0.0325% and approximately 0.0425% triamcinolone by weight, or between approximately 0.0275% and approximately 0.0350% triamcinolone by weight; between approximately 10% and approximately 35% urea by weight and between approximately 0.0350% and approximately 0.0488% triamcinolone by weight, between approximately 0.0250% and approximately 0.0375% triamcinolone by weight, between approximately 0.0325% and approximately 0.0425% triamcinolone by weight, or between approximately 0.0275% and approximately 0.0350% triamcinolone by weight; between approximately 15% and approximately 25% urea by weight and between approximately 0.0350% and approximately 0.0488% triamcinolone by weight, between approximately 0.0250% and approximately 0.0375% triamcinolone by weight, between approximately 0.0325% and approximately 0.0425% triamcinolone by weight, or between approximately 0.0275% and approximately 0.0350% triamcinolone by weight; between approximately 25% and approximately 40% urea by weight and between approximately 0.0350% and approximately 0.0488% triamcinolone by weight, between approximately 0.0250% and approximately 0.0375% triamcinolone by weight, between approximately 0.0325% and approximately 0.0425% triamcinolone by weight, or between approximately 0.0275% and approximately 0.0350% triamcinolone by weight; or between approximately 30% and approximately 50% urea by weight and between approximately 0.0350% and approximately 0.0488% triamcinolone by weight, between approximately 0.0250% and approximately 0.0375% triamcinolone by weight, between approximately 0.0325% and approximately 0.0425% triamcinolone by weight, or between approximately 0.0275% and approximately 0.0350% triamcinolone by weight.

In various embodiments, the compounded composition is provided in a kit for treating a hyperkeratotic skin condition including a capsule containing urea powder and a commercially available corticosteroid topical composition comprising triamcinolone, e.g., cream or ointment, that may be compounded proximate to the time of administration by a patient, caregiver, or medical professional. In one example, the kit includes a capsule comprising a suitable amount of urea powder to mix with the topical triamcinolone composition to obtain the desired weight percent composition. For example, a kit for treating a hyperkeratotic skin condition may include a capsule comprising a suitable amount of urea powder and a suitable amount of a topical corticosteroid composition to formulate a compounded topical composition comprising approximately 20% urea and approximately 0.08% triamcinolone. According to one example, the kit includes a dosage unit for formulating the compounded composition comprising a capsule containing 500 mg urea powder and 2 g of a 0.1% topical triamcinolone composition, e.g., Triamcinolone Acetonide Cream USP, 0.1%. In another example, a kit for treating a hyperkeratotic skin condition may include a capsule comprising a suitable amount of urea powder and a suitable amount of a topical corticosteroid composition to formulate a compounded topical composition comprising approximately 16.67% urea and approximately 0.0417% triamcinolone. According to one example, the kit includes a dosage unit for formulating the compounded composition comprising a capsule containing 500 mg urea powder and 2.5 g of a 0.05% topical triamcinolone composition, e.g., Triamcinolone Acetonide Ointment, 0.05%. In another example, a kit for treating a hyperkeratotic skin condition may include a capsule comprising a suitable amount of urea powder and a suitable amount of a topical corticosteroid composition to formulate a compounded topical composition comprising approximately 15.625% urea and approximately 0.0844% triamcinolone. According to one example, the kit includes a dosage unit for formulating the compounded composition comprising a capsule containing 500 mg urea powder and 2.7 g of a 0.1% topical triamcinolone composition, e.g., Triamcinolone Acetonide Cream USP, 0.1%. The topical triamcinolone composition may be packaged in specific dosage weights or may be provided in multi-dose packaging, e.g., 160 g, 150 g, 120 g, 100 g, 60 g, 30 g, 15 g tubes. In one embodiment, a kit may include urea cream and a topical triamcinolone composition, e.g., Triamcinolone Acetonide Cream USP, 0.1% or Triamcinolone Acetonide Ointment USP, 0.05%. The urea cream may be a compounded or commercially available urea cream. Additional actives or inactives may also be included in the kit. The kit may include a container for mixing. A stirrer may also be included. For example, the kit may include an ointment jar and a sterile swab for mixing prior to use.

In various embodiments, the compounded topical composition as described herein comprises active agents in addition to urea and a corticosteroid. For example, the compounded composition may comprise an additional active agent comprising an antibiotic agent. The antibiotic agent may comprise one or more antibiotic actives comprising amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, colistimethate teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, colimycin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, metronidazole, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, chlorhexidine, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, meropenem, or combination thereof. The compounded topical composition may comprise approximately 0.5% to 5% antibiotic by weight, such as between approximately 2.0% and approximately 5.0% antibiotic by weight. In some embodiments, larger amounts of antibiotic agent may be included, such as between 5% and 25%.

In any of the above or another embodiment, the compounded topical composition may comprise an additional active agent comprising an antifungal agent. In one example, the antifungal agent may comprise an antifungal agent comprising an azole selected from itraconazole, clotrimazole, econazole, oxiconazole, ketoconazole, miconazole, voriconazole, sulconazole, or fluconazole, ciclopirox, amphotericin B, Nystatin, terbinafine, amorolfine, flucytosine, or combinations thereof. Other antifungal agents may be used. The compounded topical composition may comprise approximately 0.5% to 5% antifungal by weight, such as between approximately 2.0% and approximately 5.0% antifungal by weight. In some embodiments, larger amounts of antifungal agent may be included, such as between 5% and 25%.

In any of the above or another embodiment, the compounded topical composition may comprise an additional active agent comprising a local anesthetic agent. The local anesthetic agent may comprise one or more local anesthetic actives selected from lidocaine, amethocaine, benzocaine, prilocaine, or combination thereof. In one formulation, the compounded topical composition comprises between approximately 0.5% to approximately 5.0% local anesthetic agent by weight.

In any of the above or another embodiment, the compounded topical composition comprises an additional active agent comprising a non-steroidal anti-inflammatory (NSAID) agent. The NSAID agent may comprise one or more NSAID actives selected from indomethacin, ibuprofen, dexibuprophen, diclofenac, ketoprofen, flurbiprofen, piroxicam, pranoprofen lidocaine, amethocaine, benzocaine, prilocaine, or combination thereof. In one formulation, composition may comprise approximately 0.5% to approximately 5.0% NSAID agent by weight. In some embodiments, larger amounts of NSAID agent may be included, such as between 5% and 25%.

It is to be understood that the above topical corticosteroid compositions or compounded topical composition formulated utilizing topical corticosteroid compositions according to the present disclosure may be diluted or cut prior to or, in some embodiments, after compounding or otherwise combining with urea, e.g., urea powder, solution, or topicals, and/or additional actives.

In various embodiments, the high potency corticosteroid may be included in the compounded topical composition in the form of a compounded corticosteroid topical, e.g., cream, ointment, foam, lotion, emulsion, spray/solution. For example, high potency corticosteroid may be added to a base (such as a commercially available base) in order to form a compounded topical composition. The base may be suitable topical base, such as the bases discussed above with regard to the compounded topical urea.

Methods

A method of making the compounded topical composition may comprise mixing urea powder and a high potency corticosteroid. The method may include releasing contents of a capsule containing urea powder and combining the urea powder contents with the high potency corticosteroid, such as any such high potency corticosteroid topical compositions described herein. For example, the high potency corticosteroid may comprise a commercially available corticosteroid topical composition. A method of making the compounded topical composition may comprise mixing one or more excipients or additives with the compounded composition. Excipients or additives may include, but are not limited to, solvents, surfactants, humectants, preservatives, flavorings, stabilizers (including antioxidants), binders, and colorants.

A method of making the compounding topical composition may comprise mixing a therapeutically effective amount of one or more additional active agents with the compounded composition. Additional active agents may include antibiotic agents, antifungal agents, local anesthetic agents, or NSAID agents for example.

The components to be compounded may be packaged separately for compounding at time or just prior to use. The compounded composition may be packaged in a compounded or partially compounded format suitable for stable storage prior to administration.

The mixing can comprise combining components within a container and stirring or folding the combined components into a homogenous mixture. For example, mixing may include stirring or folding urea powder into a commercially available corticosteroid composition, such as any corticosteroid composition described herein. In some embodiments, urea or corticosteroid may be provided in a capsule format for mixing with a commercial corticosteroid composition at the time of or prior to administration. For example, one or more capsules of urea powder may be combined with a commercial corticosteroid cream, ointment, lotion, gel, foam, spray/solution and mixed. In another embodiment, mixing may comprise using an electronic mortar and pestle (EMP). In one method a homogenous compounded composition may be mixed by milling (using, for example, a three-roll mill). Mixing and milling can be done according to standards known to the skilled person in the art. Generally, to make the compounded composition, corticosteroid and urea may be combined and mixed together using, for example, an electronic mortar and pestle (EMP). The EMP can be the Unguator 2100 or a similar device as recognized by the skilled person in the art. The compounded composition can be mixed at least one time using the "normal" (or a comparable) setting. Then, the compounded topical composition can be milled to achieve the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

In various embodiments, a method of treating a hyperkeratotic skin condition comprises dispensing the components of the compounded topical composition for subsequent compounding to treat the hyperkeratotic skin condition. For example, a method of treating a hyperkeratotic skin condition may comprise assembling or dispensing a kit for treating a hyperkeratotic skin condition including a capsule containing urea powder and a commercially available corticosteroid topical composition. According to one embodiment, a method of treating a hyperkeratotic skin condition may comprises assembling a kit comprising encapsulating urea bulk powder and providing the capsule and a commercially available topical corticosteroid composition within the kit. In one example, the corticosteroid topical composition is selected from Clobetasol Propionate Cream, Foam, Gel, or Ointment, Diflorasone Diacetate Cream or Ointment, Amcinonide Cream, Lotion, or Ointment, Betamethasone Dipropionate Cream, Lotion, Gel, or Ointment, Desoximetasone Cream or Ointment, Fluocinonide Cream, Fluocinonide Cream, Ointment, or Gel, Halcinonide Cream or Ointment, Betamethasone Valerate Cream, Lotion, or Ointment, Diflorasone Diacetate Cream or Ointment, Triamcinolone Acetonide Cream or Ointment, Halobetasol Propionate Cream, Lotion, or Ointment, Desoximetasone Cream, Gel, or Ointment, Mometasone Furoate Cream or Ointment, Fluticasone Propionate Cream, Flurandrenolide Cream, Lotion, or Ointment, or combination thereof. In another example, the corticosteroid topical composition is selected from Clobetasol Propionate Cream or Ointment, Diflorasone Diacetate Cream or Ointment, Amcinonide Cream or Ointment, Betamethasone Dipropionate Cream or Ointment, Desoximetasone Cream or Ointment, Fluocinonide Cream or Ointment, Halcinonide Cream or Ointment, Triamcinolone Acetonide Cream or Ointment, Halobetasol Propionate Cream or Ointment, Mometasone Furoate Cream or Ointment, Flurandrenolide Cream or Ointment, or combination thereof. In still another example, the corticosteroid topical composition is selected from Clobetasol Propionate Cream or Ointment, Fluocinonide Cream or Ointment, Halobetasol Propionate Cream, or Desoximetasone Cream or Ointment, Triamcinolone Acetonide Cream or Ointment, Betamethasone Dipropionate Cream or Ointment, or combination thereof. In another example of the above, the corticosteroid topical composition is selected from Clobetasol Propionate Cream, Foam, Gel, or Ointment, 0.05%, Diflorasone Diacetate Cream or Ointment, 0.05%, Amcinonide Cream, Lotion, or Ointment, 0.1%, Betamethasone Dipropionate Cream, Lotion, Gel, or Ointment 0.05%, Desoximetasone Cream or Ointment 0.25%, Fluocinonide Cream 0.1%, Fluocinonide Cream, Ointment, or Gel, 0.05%, Halcinonide Cream or Ointment, 0.1%, Betamethasone Valerate Cream, Lotion, or Ointment 0.1%, Diflorasone Diacetate Cream or Ointment, 0.05%, Triamcinolone Acetonide Cream or Ointment, 0.1%, Triamcinolone Acetonide Ointment, 0.05%, Halobetasol Propionate Cream, Lotion, or Ointment, 0.05%, Desoximetasone Cream, Gel, or Ointment 0.05%, Mometasone Furoate Cream or Ointment, 0.1%, Fluticasone Propionate Cream, 0.05%, Flurandrenolide Cream, Lotion, or Ointment, 0.05%, or combination thereof. In still a further example of the above, the corticosteroid topical composition is selected from Clobetasol Propionate Cream or Ointment, 0.05%, Diflorasone Diacetate Cream or Ointment, 0.05%, Amcinonide Cream or Ointment, 0.1%, Betamethasone Dipropionate Cream or Ointment 0.05%, Desoximetasone Cream or Ointment 0.25%, Fluocinonide Cream 0.1%, Fluocinonide Cream or Ointment, 0.05%, Halcinonide Cream or Ointment, 0.1%, Diflorasone Diacetate Cream or Ointment, 0.05%, Triamcinolone Acetonide Cream, 0.1%, Halobetasol Propionate Cream or Ointment, 0.05%, Desoximetasone Cream or Ointment 0.05%, Mometasone Furoate Cream or Ointment, 0.1%, or Flurandrenolide Cream or Ointment, 0.05%, or combination thereof. In still a further embodiment, the corticosteroid topical composition is selected from Betamethasone Dipropionate Cream or Ointment 0.05%, Clobetasol Propionate Cream or Ointment, 0.05%, Desoximetasone Cream or Ointment 0.25%, Fluocinonide Cream 0.1%, Fluocinonide Cream or Ointment, 0.05%, Triamcinolone Acetonide Cream, 0.1%, Halobetasol Propionate Cream, 0.05%, or Desoximetasone Cream or Ointment 0.05%, or combination thereof.

The kit may include one or more capsules containing urea powder and one or more containers containing a commercially available topical corticosteroid composition comprising a high potency corticosteroid, such as those described above and elsewhere herein. The kit may include a container for mixing. A stirrer may also be included. For example, the kit may include an ointment jar and a sterile swab for mixing prior to administration.

In one example, a kit includes one or more capsules containing urea powder and one or more containers containing a commercially available topical corticosteroid composition comprising Fluocinonide Cream, 0.1%. A method of treating a hyperkeratotic skin condition utilizing the kit may include assembling or dispensing the kit or compounding the urea powder and Fluocinonide Cream, 0.1%, to formulate a compounded topical composition comprising approximately 20% urea and approximately 0.08% fluocinonide. For example, the kit may include instructions for combining 500 mg urea powder contained within a capsule with 2 grams of the Fluocinonide Cream, 0.1%. In another embodiment, a method of treating a hyperkeratotic skin condition utilizing a kit may include assembling or dispensing the kit or compounding the urea powder and Halobetasol Cream, 0.05%, provided with the kit to formulate a compounded topical composition comprising approximately 16.67% urea and approximately 0.0417% halobetasol. For example, the kit may include instructions for combining 500 mg urea powder contained within a capsule with 2.5 grams of the Halobetasol Cream, 0.05%. Other amounts of commercially available topical corticosteroid compositions may be used such as between 0.5 g and 6 g. Other amounts of urea powder may be used such as between 5 mg and 1000 mg. In various embodiments, a method of treating a hyperkeratotic skin condition utilizing a kit may include assembling or dispensing the kit or compounding the urea powder and a commercial topical corticosteroid composition comprising any commercial topical corticosteroid composition described herein provided with the kit for treating hyperkeratotic skin conditions according to any method disclosed herein. The kit may also include inactive agents or additional active agents as described herein. For example, the method may include assembling a kit, dispensing a kit, or making the compounded topical composition from kit components as described herein including providing with the kit or combining with the urea and commercially available topical corticosteroid composition an additional active agent consistent with this disclosure selected from an antibacterial agent, an antiviral agent, an antifungal agent, an antibiotic agent, an anti-inflammatory agent, an non-steroidal anti-inflammatory (NSAID) agent, an anti-allergic agent, an anti-infective agent, an anti-depressant agent, an additional steroid agent, a stimulant agent, a disinfectant agent, an anticonvulsant agent, a local anesthetic agent, or combinations thereof.

The user may be directed to compound or apply the compounded topical composition to an affected area 1-4 times a day, such as 1, 2, 3, or 4 times a day, for example. A dressing may be applied over the application area. A dressing may be provided in the kit.

The capsules and containers containing the high potency corticosteroid may be provided in individual packaging for convenient mixing. For example, the capsules and container, such as a tube or jar, may be provided in single dose capsules and containers. Tubes, for example, may contain premeasured amounts of the topical composition thereby allowing the user to combine the proper weight percent of each of urea powder and topical corticosteroid composition when mixing a dose. In some embodiments, the containers may contain multiple doses. In a further embodiment, the topical corticosteroid is provided in a tube that includes a plunger, e.g., configured similar to a syringe, wherein a user may actuate the plunger to a marked position on the tube to eject an amount of the contained topical composition from the tube for formulating the dose.

A method of making the topical composition comprising a compounded topical cream including urea and high potency corticosteroid, as described herein, may include combining urea powder with a commercially available topical corticosteroid composition, which may include compounding the contents of a kit for the treatment of a hyperkeratotic skin condition. In various embodiments, the method comprises combining urea powder with a commercially available topical corticosteroid composition in suitable amounts such that the compounded topical composition comprises any percent composition disclosed herein. For example, the method may include combining urea powder with a commercially available topical corticosteroid composition in suitable amounts such that the compounded topical composition comprises between In various embodiments, the method comprises combining urea powder and the topical corticosteroid composition in an amount wherein the compounded topical composition comprises between approximately 2.5% and approximately 50% urea by weight and between approximately 0.001% and approximately 0.5% of the selected high potency corticosteroid by weight, which in some embodiments may include multiple high potency corticosteroids in combination, such as between approximately 2.5% and approximately 25% urea by weight and between approximately 0.025% and approximately 0.100% high potency corticosteroid by weight, between approximately 10% and approximately 35% urea by weight and between approximately 0.025% and approximately 0.100% high potency corticosteroid by weight, between approximately 15% and approximately 25% urea by weight and between approximately 0.025% and approximately 0.100% high potency corticosteroid by weight, between approximately 25% and approximately 40% urea by weight and between approximately 0.025% and approximately 0.100% high potency corticosteroid by weight, between approximately 30% and approximately 50% urea by weight and between approximately 0.025% and approximately 0.100% high potency corticosteroid by weight, between approximately 2.5% and approximately 25% urea by weight and between approximately 0.05% and approximately 0.1% high potency corticosteroid by weight, between approximately 10% and approximately 35% urea by weight and between approximately 0.05% and approximately 0.1% high potency corticosteroid by weight, between approximately 15% and approximately 25% urea by weight and between approximately 0.05% and approximately 0.1% high potency corticosteroid by weight, between approximately 25% and approximately 40% urea by weight and between approximately 0.05% and approximately 0.1% high potency corticosteroid by weight, between approximately 30% and approximately 50% urea by weight and between approximately 0.05% and approximately 0.1% high potency corticosteroid by weight, between approximately 2.5% and approximately 25% urea by weight and between approximately 0.03% and approximately 0.05% high potency corticosteroid by weight, between approximately 10% and approximately 35% urea by weight and between approximately 0.03% and approximately 0.05% high potency corticosteroid by weight, between approximately 15% and approximately 25% urea by weight and between approximately 0.03% and approximately 0.05% high potency corticosteroid by weight, between approximately 25% and approximately 40% urea by weight and between approximately 0.03% and approximately 0.05% high potency corticosteroid by weight, between approximately 30% and approximately 50% urea by weight and between approximately 0.03% and approximately 0.05% high potency corticosteroid by weight, between approximately 2.5% and approximately 25% urea by weight and between approximately 0.05% and approximately 0.085% high potency corticosteroid by weight, between approximately 10% and approximately 35% urea by weight and between approximately 0.05% and approximately 0.085% high potency corticosteroid by weight, between approximately 15% and approximately 25% urea by weight and between approximately 0.05% and approximately 0.085% high potency corticosteroid by weight, between approximately 25% and approximately 40% urea by weight and between approximately 0.05% and approximately 0.085% high potency corticosteroid by weight, between approximately 30% and approximately 50% urea by weight and between approximately 0.05% and approximately 0.085% high potency corticosteroid by weight.

In various examples of the above embodiments, the method comprises combining a suitable amount of urea with the topical corticosteroid composition to achieve a weight percent of urea with respect to the compounded topical composition between 5% and 50% urea, such as approximately 7%, approximately 9%, approximately 11%, approximately 13%, approximately 14%, approximately 15%, approximately 16%, approximately 17%, approximately 19%, approximately 20%, approximately 21%, approximately 22%, approximately 23%, approximately 24%, approximately 25%, approximately 27%, approximately 29%, approximately 31%, approximately 35%, approximately 39%, approximately 43%, approximately 47%, approximately 50%, less than approximately 40%, less than approximately 30%, less than approximately 25%, less than approximately 20%, or less than approximately 15%. The method may further comprise combining a suitable amount of the topical corticosteroid composition with the urea powder to achieve any of the above weight percentages of urea such that the compounded topical composition further comprises between approximately 0.001% and approximately 0.5% of the selected high potency corticosteroid by weight, which in some embodiments may include multiple high potency corticosteroids in combination, such as approximately 0.005%, approximately 0.01%, approximately 0.02%, approximately 0.03%, approximately 0.04%, approximately 0.045%, approximately 0.05%, approximately 0.055%, approximately 0.06%, approximately 0.065%, approximately 0.07%, approximately 0.075%, approximately 0.08%, approximately 0.085%, approximately 0.09%, approximately 0.095%, approximately 0.1%, approximately 0.2%, approximately 0.3%, approximately 0.4%, approximately 0.5%, less than approximately 0.2%, less than approximately 0.1%, less than approximately 0.09%, less than approximately 0.08%, less than approximately 0.07%, less than approximately 0.06%, less than approximately 0.05%, less than approximately 0.04%, less than approximately 0.03%, less than approximately 0.02%, or less than approximately 0.01%.

The high potency corticosteroid or compounded topical composition may be further supplemented with urea or high potency corticosteroid in other formats, diluted, or cut prior to or, in some embodiments, after mixing of the high potency corticosteroid and urea or one or more additional active ingredients or inactive ingredients.

A method of treating a hyperkeratotic skin condition may also comprise administering the compounded topical composition according to the present disclosure.

As noted above, the compounded topical composition, kit for making the compounded topical composition, may also contain urea sources other than or instead urea powders, such as commercial or compounded urea creams, lotions, emulsions, solutions, ointments, or gels. Thus, the amount of urea powder or other sourced urea may be adjusted to obtain the final weight percentages of fluocinonide in compounded topical composition by methods described herein or otherwise known in the art. Similarly, the topical compounded cream may also contain high potency corticosteroid from sources other than commercial topical corticosteroid compositions, such as from bulk powders, ground oral tablets, or solutions. Thus, the amount of high potency corticosteroid may be adjusted to obtain the final weight percentages of fluocinonide in compounded topical composition by methods described herein or otherwise known in the art.

The method of making the compounded topical composition may further comprise an addition of one or more additional inactive agents, e.g., emollients, or active agents. Additional active agents may be combined with urea and high potency corticosteroid in powder form, such as ground oral tablets or bulk powder, in solution, cream, lotion, ointment, gel, emulsion, or combinations thereof. In various embodiments, additional active agents may together comprise between approximately 1% to approximately 15% by weight of the compounded topical composition. Additional active agents may be selected from an antibacterial agent, an antiviral agent, an antifungal agent, an antibiotic agent, an anti-inflammatory agent, an non-steroidal anti-inflammatory (NSAID) agent, an anti-allergic agent, an anti-infective agent, an anti-depressant agent, an additional steroid agent, a stimulant agent, a disinfectant agent, an anticonvulsant agent, a local anesthetic agent, or combinations thereof.

In one embodiment wherein the topical composition includes an additional active agent, the composition comprises between approximately 0.5% and 2.5% by weight of a steroid agent selected from fluticasone, triamcinolone, betamethasone, dexamethasone, flunisolide, prednisone, prednisolone, methylprednisolone, fluocinolone, diflorasone, halcinonide, desoximetasone, diflucortolone, flucloronide, fluocortolone, fluprednidene, flurandrenolide (flurandrenolone), clobetasol, clobetasone, alclometasone, flumethasone, fluocortolone, amcinonide, beclometasone, difluprednate, prednicarbate, flurandrenolide, mometasone, desonide, or combinations thereof. In one embodiment, the steroid agent is or comprises fluticasone wherein the cream comprises approximately 0.5% to approximately 1.5% by weight fluticasone.

In a further embodiment the method may include adding an additional active agent comprising an antifungal agent or an antibiotic agent such that the compounded topical composition comprises between approximately 1.5% to approximately 6.0% by weight of either or both of (a) an antifungal agent comprising an azole selected from itraconazole, clotrimazole, econazole, oxiconazole, ketoconazole, miconazole, voriconazole, sulconazole, or fluconazole, ciclopirox, amphotericin B, Nystatin, terbinafine, amorolfine, flucytosine, or combinations thereof, and (b) an antibiotic agent selected from amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, colistimethate teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, colimycin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, metronidazole, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, chlorhexidine, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, meropenem, or combination thereof.

In any of the above embodiments or a further embodiment the method may include adding an additional active agent comprising a local anesthetic or NSAID agent such that the compounded topical composition comprises approximately 0.5% to approximately 5.0% by weight of either or both of (a) a local anesthetic agent selected from lidocaine, amethocaine, or combinations thereof, and (b) a non-steroidal anti-inflammatory (NSAID) agent selected from indomethacin, ibuprofen, dexibuprophen, diclofenac, ketoprofen, flurbiprofen, piroxicam, pranoprofen lidocaine, amethocaine, benzocaine, prilocaine, or combinations thereof.

Methods of using the topical composition may include treating an individual in need by topically applying the cream to affected skin. Conditions treated may include conditions such as those marked by thickening of the skin, referred to as hyperkeratosis. The compounded topical composition described herein may thus be applied to such affected areas of the skin to treat the affected area. The composition may alleviate symptoms such as redness, swelling, or itching. The composition may accelerate the healing process with respect to the affected skin. In various embodiments, the topical composition may be administered to treat hyperkeratotic conditions. The hyperkeratotic skin condition treated may be chronic eczema, corns, calluses, warts, seborrheic keratosis, lichen planus, actinic keratosis, as examples. The hyperkeratotic skin conditions may be caused by irritation, such as physical pressure or rubbing, chemical, infection, sunlight or radiation, or inherited conditions, for example.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of formulating a topical composition for treatment of a hyperkeratotic skin condition, the method comprising:
   combining contents of a compounded capsule with a corticosteroid cream to formulate a topical composition for application to a skin area affected by hyperkeratosis,
   wherein the contents of the capsule comprise urea bulk powder, and
   wherein the step of combining the contents of the compounded capsule with the corticosteroid cream comprises stirring or folding the urea bulk powder into the corticosteroid cream,
   wherein the corticosteroid cream comprises Clobetasol Propionate Cream, 0.05%, comprising cetyl alcohol, citric acid, glycol stearate, lanolin oil, methylparaben, PEG-8 stearate, polysorbate 60, propylene glycol, propylparaben, purified water, sodium citrate, stearyl alcohol, and white petrolatum, and
   wherein the topical composition comprises between approximately 2.5% and approximately 50% urea by weight and between approximately 0.0250% and approximately 0.0488% clobetasol propionate by weight.

2. The method of claim 1, wherein the topical composition comprises between approximately 10% and approximately 25% urea by weight and between approximately 0.0250% and approximately 0.0375% clobetasol propionate by weight.

3. The method of claim 1, wherein the topical composition comprising between approximately 10% and approximately 25% urea by weight and between approximately 0.0325% and approximately 0.0425% clobetasol propionate by weight.

4. A method of treating a hyperkeratotic skin condition, the method comprising:
   using a kit for treatment of a hyperkeratotic skin condition, the kit comprising
      a compounded capsule containing urea bulk powder and
      a corticosteroid ointment comprising clobetasol propionate,
   stirring or folding the urea bulk powder contents of the compounded capsule with the corticosteroid ointment to formulate a topical composition comprising between approximately 2.5% and approximately 50% urea by weight and between approximately 0.0250% and approximately 0.0488% clobetasol propionate by weight, wherein the corticosteroid ointment comprises Clobetasol Propionate Ointment, 0.05%, comprising propylene glycol, sorbitan sesquioleate, and white petrolatum, and applying the topical composition to a skin area affected by hyperkeratosis.

\* \* \* \* \*